United States Patent [19]
Kablik et al.

[11] Patent Number: 5,928,257
[45] Date of Patent: Jul. 27, 1999

[54] SURGICAL IRRIGATION PUMP AND TOOL SYSTEM

[75] Inventors: Joseph J. Kablik, Los Gatos; Anthony Chikuo Lee, Santa Clara, both of Calif.

[73] Assignee: Stryker Corporation, Kalamazoo, Mich.

[21] Appl. No.: 09/093,484

[22] Filed: Jun. 8, 1998

Related U.S. Application Data

[62] Division of application No. 08/713,434, Sep. 13, 1996, Pat. No. 5,792,167.

[51] Int. Cl.$^6$ .................................................. A61B 17/14
[52] U.S. Cl. ........................................... 606/180; 604/34
[58] Field of Search ................................. 606/180, 170, 606/171, 159; 604/22, 34, 35

[56] References Cited

U.S. PATENT DOCUMENTS

| | | |
|---|---|---|
| 3,568,318 | 3/1971 | Martin . |
| 3,674,024 | 7/1972 | Cirillo . |
| 3,882,872 | 5/1975 | Douvas et al. . |
| 3,912,168 | 10/1975 | Mullins et al. . |
| 3,960,466 | 6/1976 | Taylor . |
| 3,993,054 | 11/1976 | Newman . |
| 4,138,205 | 2/1979 | Wallach . |
| 4,179,249 | 12/1979 | Guttmann . |
| 4,239,464 | 12/1980 | Hein . |
| 4,276,023 | 6/1981 | Phillips et al. . |
| 4,548,553 | 10/1985 | Ferster . |
| 4,552,516 | 11/1985 | Stanley . |
| 4,559,040 | 12/1985 | Horres et al. . |
| 4,705,038 | 11/1987 | Sjostrom et al. . |
| 4,735,558 | 4/1988 | Kienholz et al. . |
| 4,767,289 | 8/1988 | Parrott et al. . |
| 4,820,265 | 4/1989 | DeSatnick et al. . |
| 4,824,339 | 4/1989 | Bainbridge et al. . |
| 4,904,168 | 2/1990 | Cavoto et al. . |
| 4,909,713 | 3/1990 | Finsterwald et al. . |
| 4,982,739 | 1/1991 | Hemstreet et al. . |
| 4,998,527 | 3/1991 | Meyer . |
| 5,017,059 | 5/1991 | Davis . |
| 5,195,960 | 3/1993 | Hossain et al. ............................ 604/34 |
| 5,203,769 | 4/1993 | Clement et al. .......................... 604/35 |
| 5,230,614 | 7/1993 | Zanger et al. . |
| 5,256,041 | 10/1993 | Tucker . |
| 5,295,956 | 3/1994 | Bales et al. ............................. 604/35 |
| 5,399,160 | 3/1995 | Dunberger et al. . |
| 5,403,277 | 4/1995 | Dodge et al. . |
| 5,433,588 | 7/1995 | Monk et al. . |
| 5,484,402 | 1/1996 | Saravia et al. . |

FOREIGN PATENT DOCUMENTS

| | | |
|---|---|---|
| 569 875A1 | 11/1993 | European Pat. Off. . |
| 3-26887 | 2/1991 | Japan . |
| 2 076 068A | 11/1981 | United Kingdom . |
| 2 190 145 | 3/1987 | United Kingdom . |
| WO93/22560 | 11/1993 | WIPO . |

OTHER PUBLICATIONS

3M Arthroscopy Pump, 70–2008–1302–3 (39.75) TP (4 sheets).

*Primary Examiner*—Michael Buiz
*Assistant Examiner*—Kevin Truong
*Attorney, Agent, or Firm*—Flynn, Thiel, Boutell & Tanis, P.C.

[57] ABSTRACT

An irrigation surgical tool system comprises a motorized handpiece, a tool for insertion in the handpiece, a console including a mounting plate and peristaltic pump rotor and a tube set including a cassette installable on the console for peristaltic pumping of irrigation liquid to the tool. Passages in the tool allow irrigation liquid flow, between a fixed outer tube and rotating inner tube of the tool, to a surgical site, through windows in the tool inner and outer tubes. Application of suction to the tool enables withdrawal through the inner tube of irrigation and surgical debris from the surgical site.

12 Claims, 15 Drawing Sheets

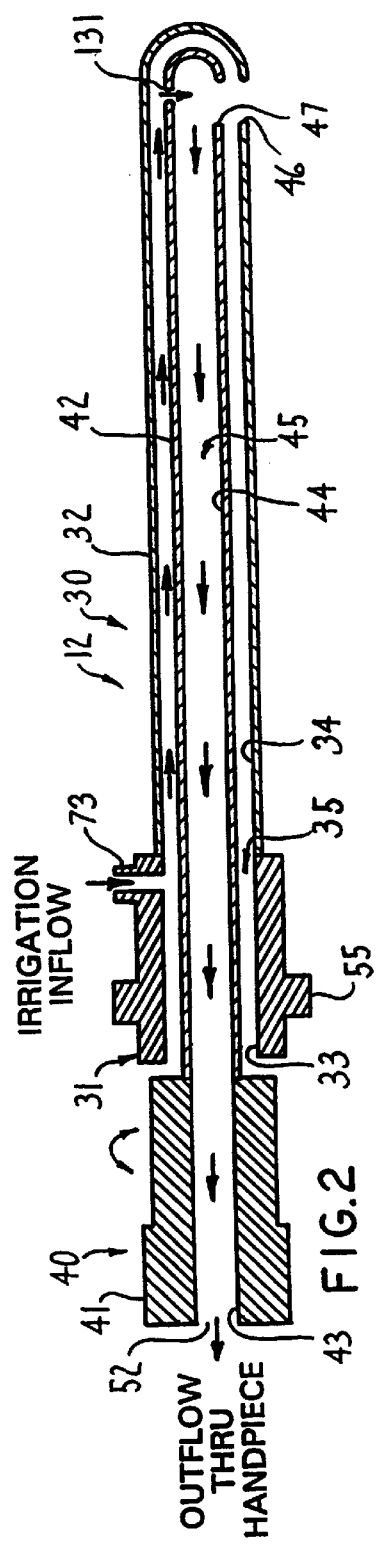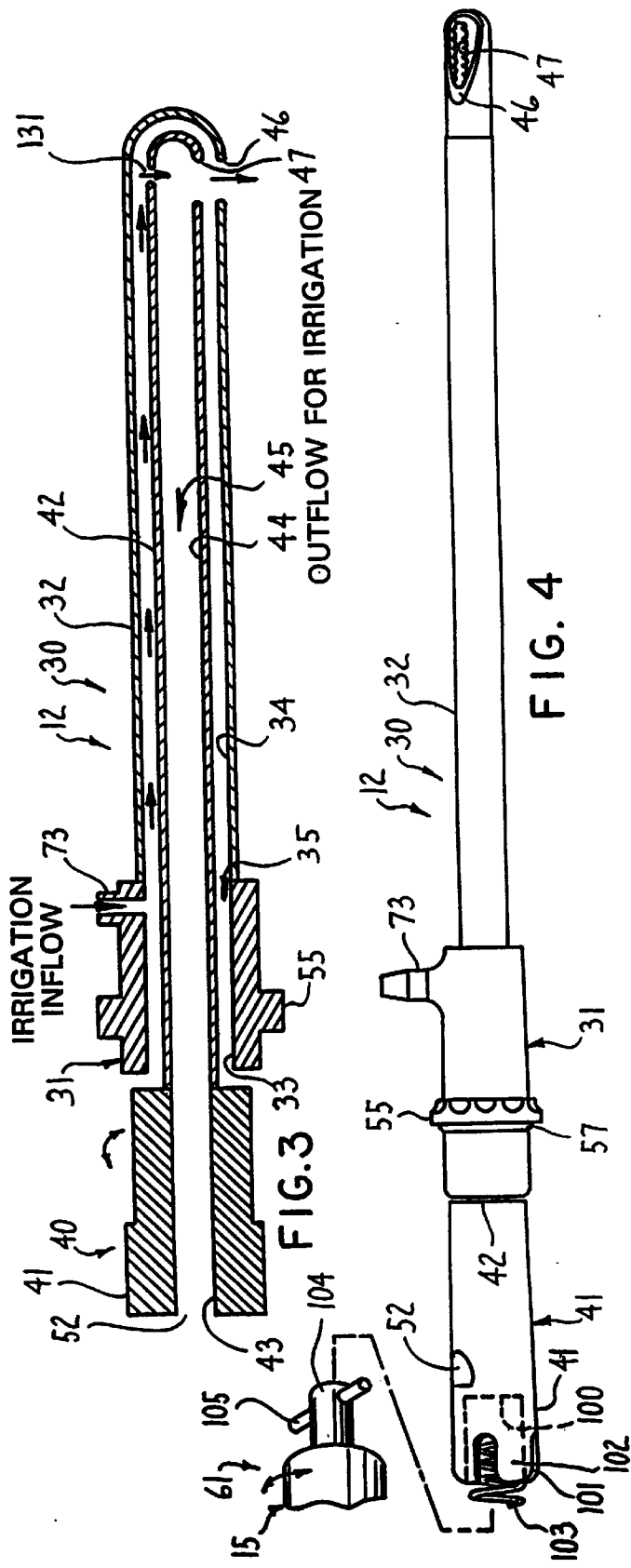

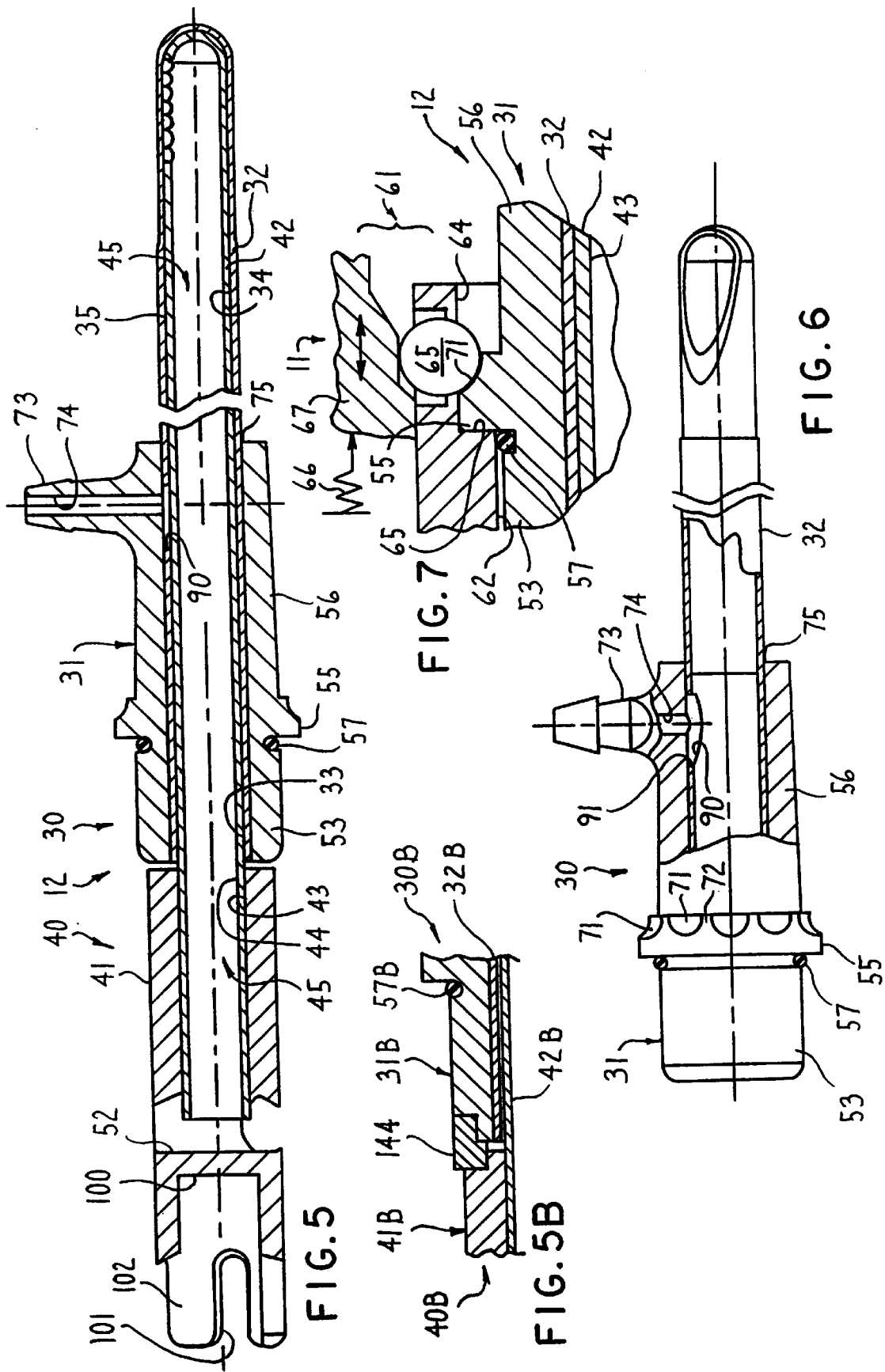

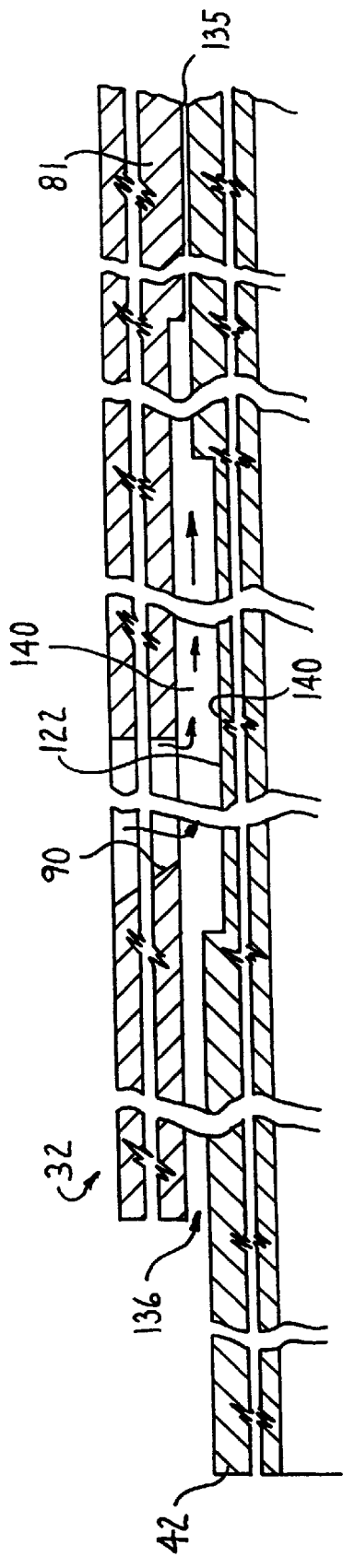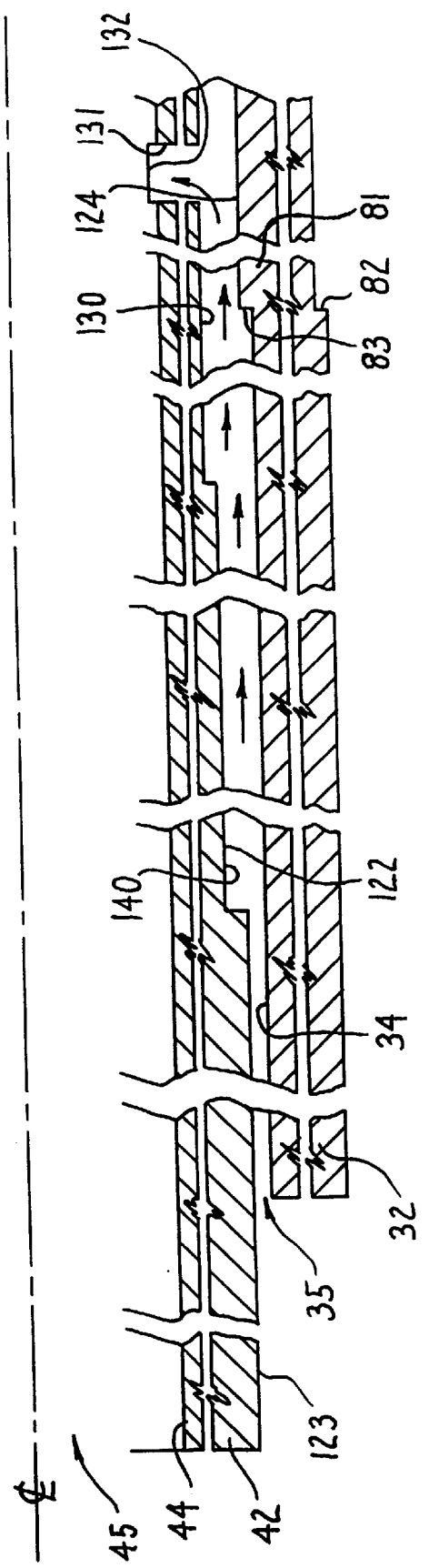
FIG. 5A

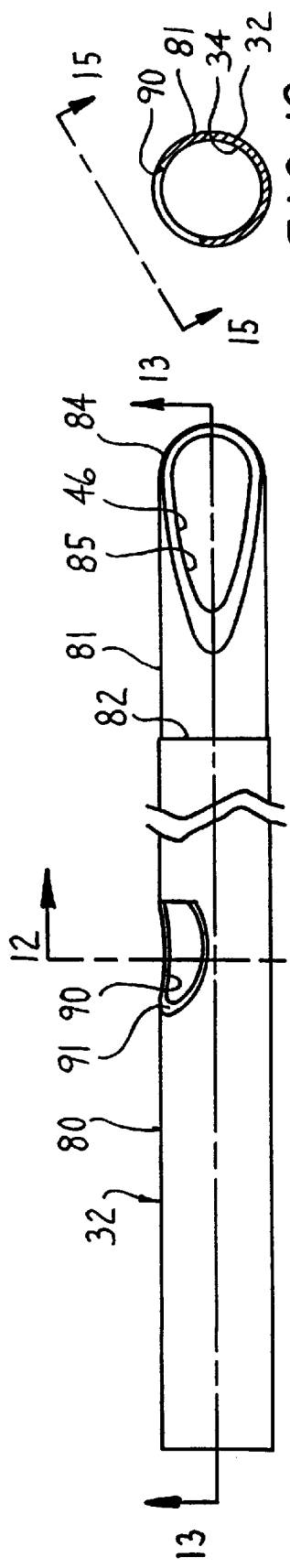
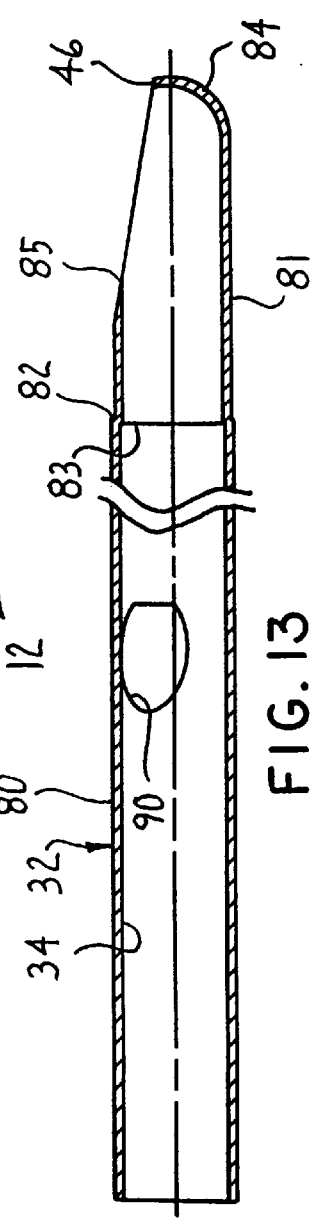
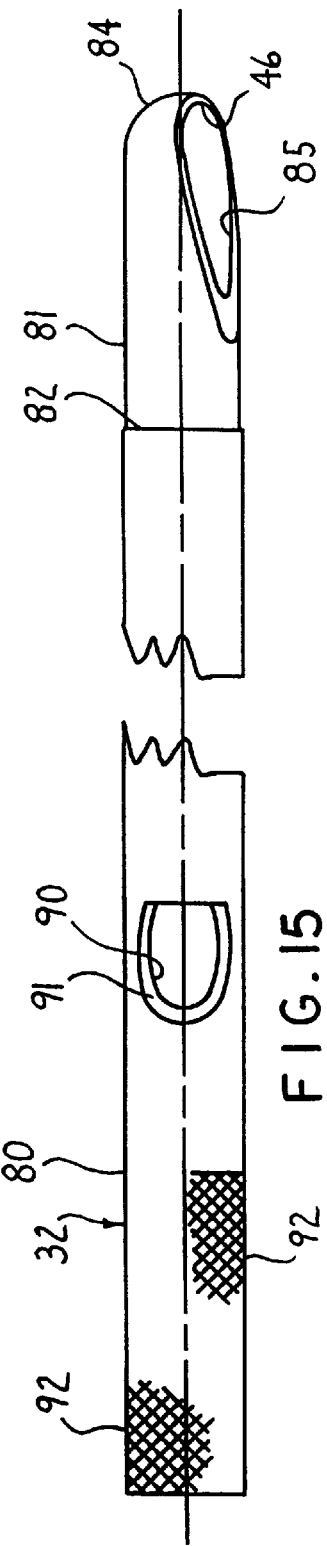

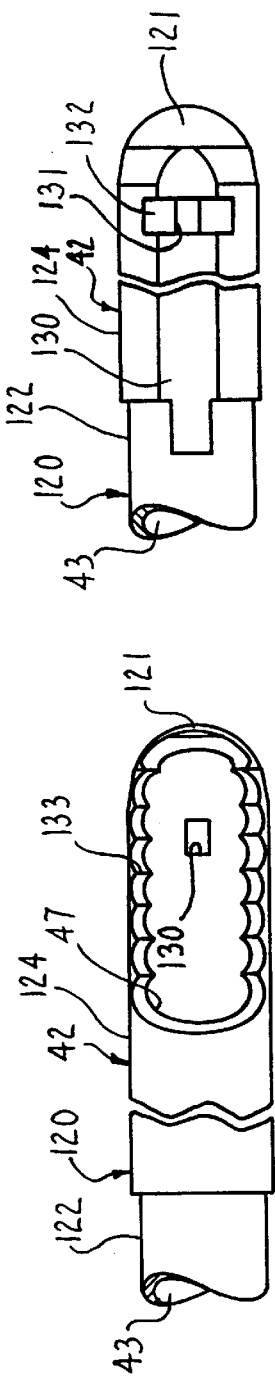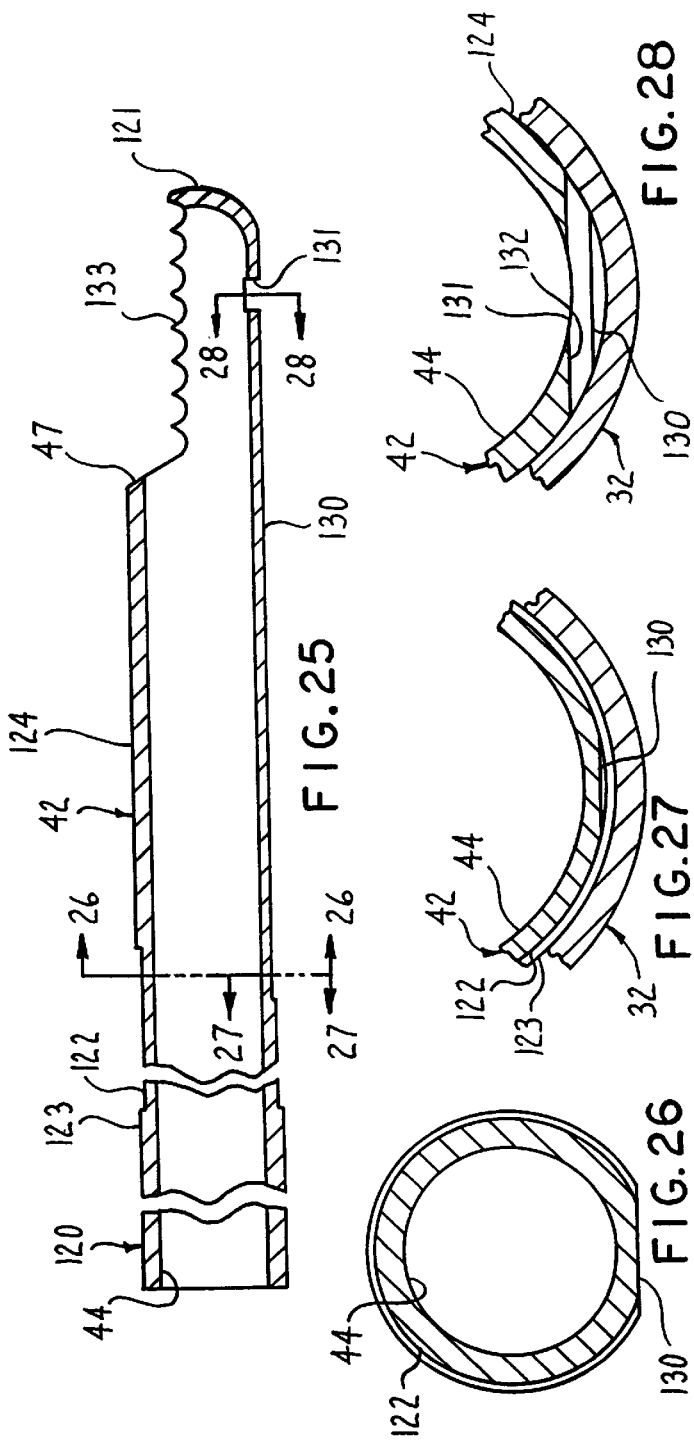

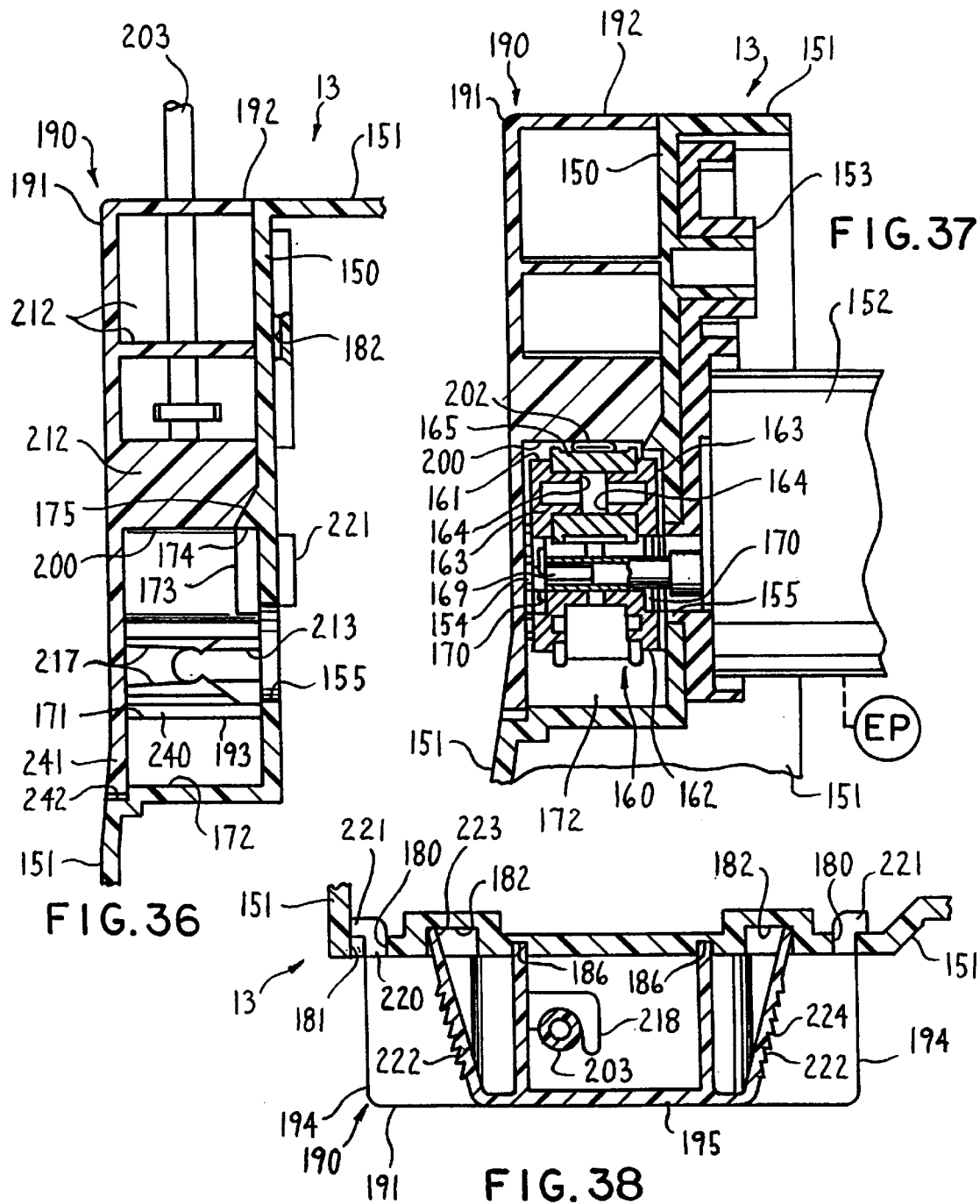

SURGICAL IRRIGATION PUMP AND TOOL SYSTEM

This is a division of Ser. No. 08/713 434, filed Sep. 13, 1996 now U.S. Pat. No. 5,792,167.

FIELD OF THE INVENTION

This invention relates to a surgical irrigation pump and tool system.

BACKGROUND OF THE INVENTION

Supplying irrigation liquid to a surgical site via a surgical handpiece from a peristaltic pump on a remote console has been long known.

However, in a continuing effort to improve on apparatus of this type, the present invention was developed.

SUMMARY OF THE INVENTION

The present invention relates in one aspect to an irrigation surgical tool system including a motorized handpiece, a tool removably insertable therein, a console including a peristaltic pump rotor and a tube set including a cassette mountable on the console for coaction with the rotor to supply irrigation liquid to the tool. The invention relates in another aspect to a tool having a rotating inner tube within a fixed outer tube. An irrigation liquid passage between the tubes communicates with the inner tube and thence through tissue working windows in the inner and outer tubes with a surgical site for alternately supplying irrigation liquid to the surgical site and removing, by entrainment, of debris from the surgical site by means of suction in the inner tube.

Further objects and purposes of the invention will be apparent to persons acquainted with apparatus of this general type upon reading the following description and inspecting the accompanying drawings.

BRIEF DESCRIPTION OF THE DRAWINGS

FIG. 2 is a schematic cross-sectional view of the cutter of FIG. 1.

FIG. 3 is a view similar to FIG. 2 with irrigation but not suction applied.

FIG. 4 is an elevational view of the FIG. 1 cutter.

FIG. 5 is an enlarged fragmentary central cross section of the FIG. 4 cutter.

FIG. 5A is a fragmentary enlargement of FIG. 5.

FIG. 5B is an enlarged fragment of FIG. 5 showing in cross-section a modified tool fragment, the modification including an annular seal interposed between the fixed and rotating hubs of the tool.

FIG. 6 is an enlarged fragmentary partially broken view of the FIG. 4 cutter.

FIG. 7 is an enlarged fragment of FIG. 5 showing in cross section a handpiece fragment for resiliently retaining the tubular mounting hub of the tubular outer housing.

FIG. 11 is a fragmentary view of the outer tube of the cutter.

FIG. 12 is a sectional view substantially taken on the line 12—12 of FIG. 11.

FIG. 13 is a central cross-sectional view substantially taken on the line 13—13 of FIG. 11.

FIG. 14 is a right end view of the FIG. 13 outer tube.

FIG. 15 is a fragmentary elevational view of the cutter outer tube of FIGS. 11–14 taken generally along the line 15—15 of FIG. 12.

FIG. 23 is an enlarged fragment of the forward end portion (rightward in FIG. 20) of the FIG. 20 and 22 rotatable inner tube.

FIG. 24 is a view similar to FIG. 23 but taken from the opposite side thereof, namely from the bottom in FIG. 20 and showing an enlarged fragment of FIG. 22.

FIG. 25 is a central cross sectional view of the FIG. 23 inner tube forward end portion taken substantially on the line 25—25 of FIG. 22.

FIG. 26 is a transverse cross sectional view substantially taken on the line 26—26 of FIG. 25.

FIG. 27 is an enlarged fragmentary transverse cross sectional view substantially taken on the line 27—27 of FIG. 25.

FIG. 28 is an enlarged fragmentary transverse cross sectional view substantially taken on the line 28—28 of FIG. 25.

FIG. 36 is a sectional view substantially taken on the line 36—36 the FIG. 35 with the cassette installed on the console.

FIG. 37 is a view similar to FIG. 36 but with a pump cassette installed in pumping position on the console mounting face.

FIG. 38 is a cross-sectional view substantially taken on the line 38—38 of FIG. 35 with the cassette installed on the console.

DETAILED DESCRIPTION

Figure 1:
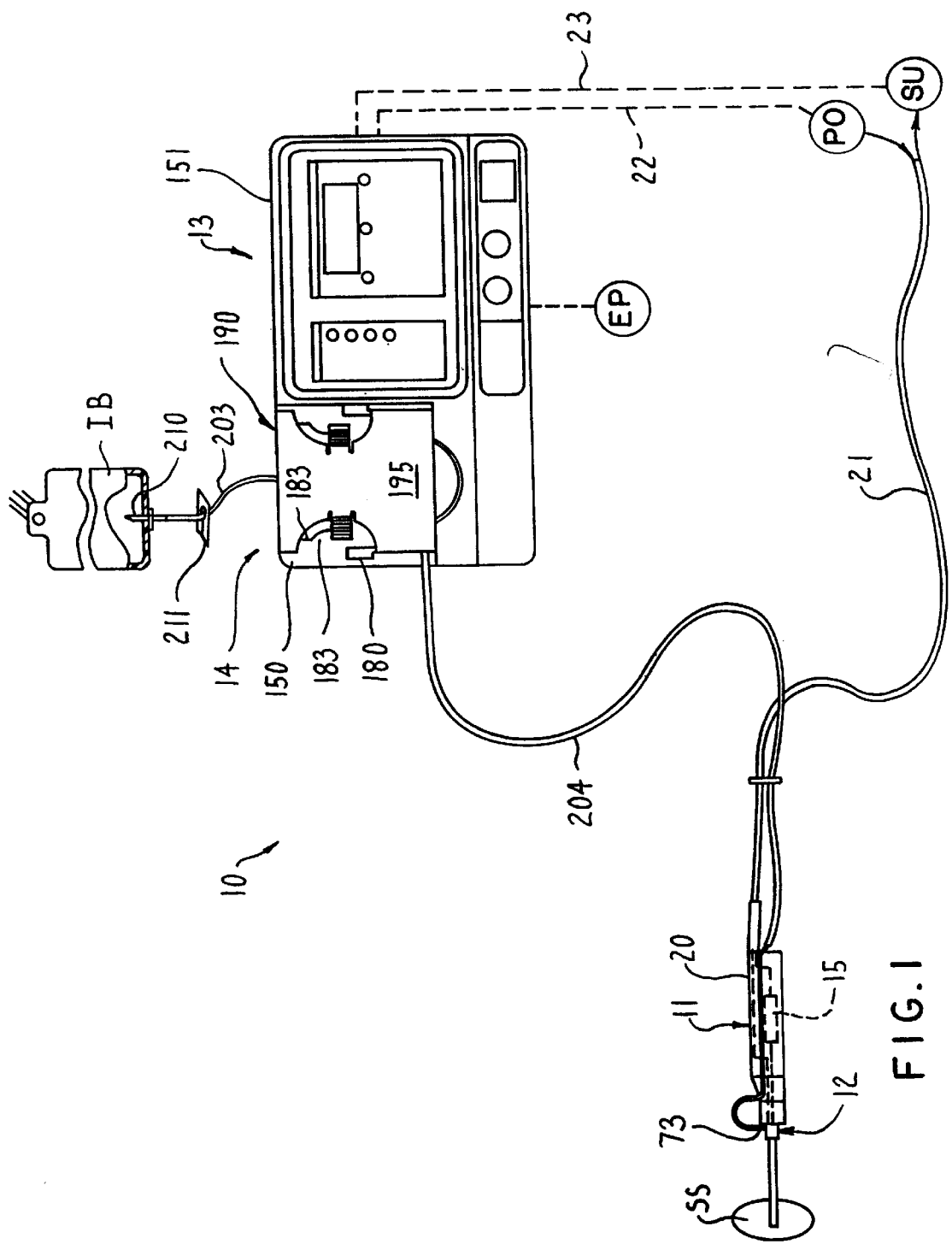
FIG. 1 is a somewhat schematic view of a surgical irrigation pump system embodying the invention.

An irrigation cutter system 10 (FIG. 1) comprises a motorized handpiece 11 removably supporting and driving a tool 12 insertable into a surgical site SS for working (e.g. cutting) patent tissue in the surgical site. The system 10 further includes a console 13 preferably located remote from the handpiece 11 and surgical site SS and a tube set 14 removably connectable with the console 13 and cooperable therewith for pumping irrigation liquid from a conventional irrigation liquid source, such as a conventional bag IB, to the handpiece 11. The handpiece 11 may be substantially conventional and, for example, similar to cutter handpieces marketed by Stryker Corporation under the trademark HUMMER I.

Figure 9:
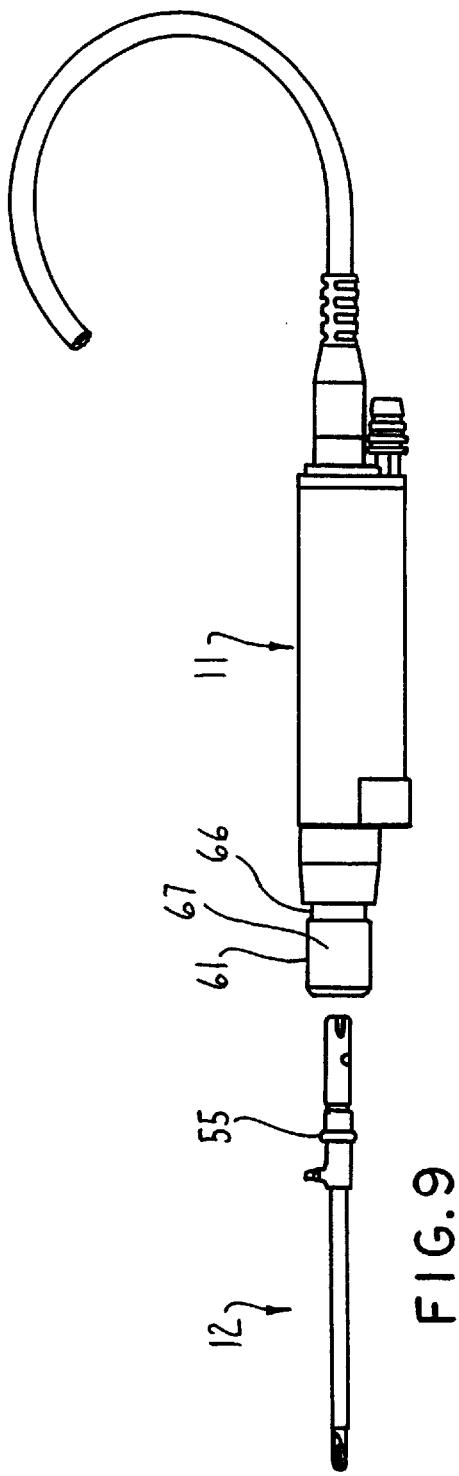
FIG. 9 is an elevational view similar to FIG. 8.
Figure 10:
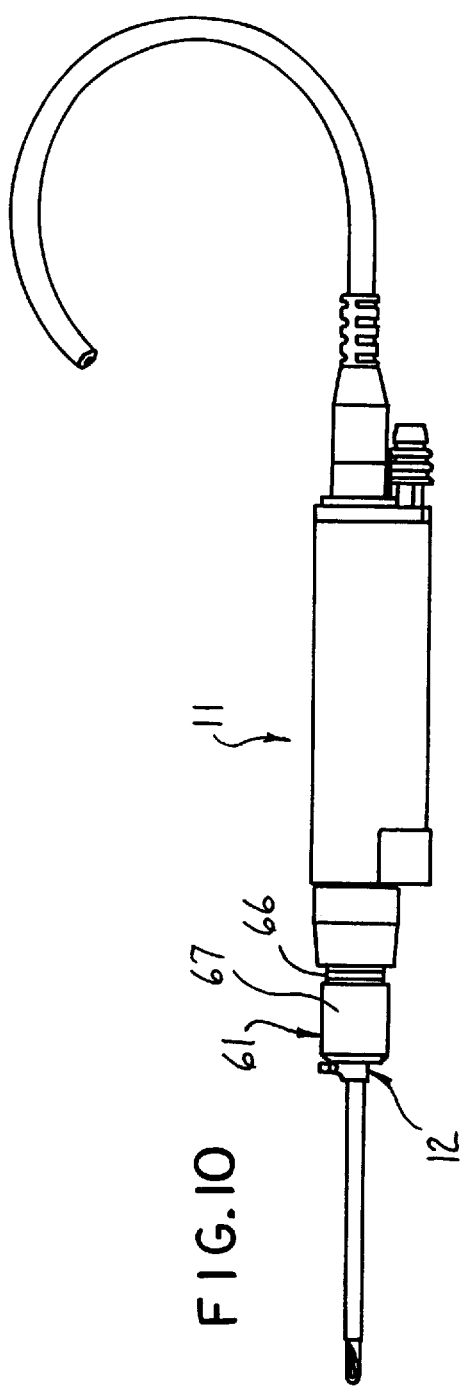
FIG. 10 is an elevational view similar to FIG. 9 but showing the cutter and handpiece engaged in an operating position.

Thus, the handpiece 11 includes a power rotation source (e.g. electric motor), 15 indicated schematically in dotted lines in FIG. 1, contained in a hand held casing 20. The handpiece is supplied operating power for its powered rotation source 15 from any convenient power source schematically indicated at PO, such as a conventional electric power source of the type used to operate conventional surgical powered handpieces. The handpiece 11 is here provided with an internal suction path by which it can apply suction to the tool 12 in a substantially conventional manner, from a suitable suction source SU, as schematically indicated in dotted line in FIG. 1. The power source PO and suction source SU may be connected to the handpiece 11 in any conventional manner, as in FIG. 1 through a common flexible cable 21 containing side by side insulated electric wires and a suction hose, not shown, or through separate flexible electrical cable and suction hose runs, as schematically indicated in FIGS. 9 and 10. The power source PO be controlled (e.g. turned on and off or varied) in any conventional manner, either directly by the user, or, as indicated schematically by the dotted line at 22, by suitable controls on the console 13 and operable by the user.

A tool 12 embodying the invention is shown in elevation in FIG. 4 and schematically in cross section in FIGS. 2 and 3. FIGS. 2 and 3 schematically show the basic parts of the tool 12. The tool 12 here comprises a tubular radially outer housing 30 including a tubular mounting hub 31 for fixed but releasable mounting on the forward portion of the casing 20 of the handpiece 11 and an outer tube 32 fixedly projecting forward from the mounting hub 31. The mounting hub and outer tube have communicating coaxial bores 33 and 34 defining a common radially outer passage 35.

The tool 12 further includes a tubular radially inner rotor 40 including a rotor hub 41 rotatably drivable by the power rotation source 15 of the handpiece 11 (FIG. 1), and an inner tube 42 fixedly projecting forward from the rotor hub 41. The rotor hub and inner tube have communicating coaxial bores 43 and 44 defining a common radially inner fluid passage 45.

The inner tube 42 is rotatably housed in the outer tube 32 and associated outer tubular mounting hub 31, extending axially from substantially the front (right in FIGS. 2 and 3) end of the outer tube 32 rearwardly (leftwardly in FIGS. 2 and 3) to the outer tubular mounting hub 31, to coaxially fixedly engage the rotor hub 41.

Although it is contemplated that the present invention may be applicable to surgical tools of different kind, in the particular embodiment shown the forward ends of the outer and inner tubes are at least partially closed (here providing an end thrust bearing effect therebetween), and the front end portions of such outer and inner tubes are each provided with sidewardly and/or radially opening, circumferentially alignable, patient tissue engaging windows, namely an outer window 46 and an inner window 47. In the particular embodiment shown, at least one window 46 or 47 has a cutting edge for cutting patient tissue upon rotation of the inner tube 42 within the outer tube 32. The rotation of the inner tube with respect to the outer tube thus periodically substantially radially aligns the inner window 47 with the outer window 46 and allows, at that time, communication between the inner fluid passage 45 and outer window 46.

The rotor hub 41, as schematically shown in FIGS. 2 and 3, has a hole 52 opening from the bore 43 which communicates through the handpiece 11 with the suction source SU as schematically shown in, and discussed above with respect to, FIG. 1.

To the extent above described, the tool 12, in its embodiment here shown, is substantially similar to conventional endoscopic suction cutters.

Turning now in more detail to the hollow outer housing 30, its mounting hub 31 (FIGS. 6 and 16–18) is conveniently constructed as a molded plastics member and is substantially rigid. The mounting hub 31 externally comprises a substantially cylindrical rear portion 53, an annular groove 54, a circumferential rib 55 and an elongate, somewhat forwardly tapering, forward portion 56. The annular groove 54 is occupied by a resilient seal ring, here a conventional O-ring 57, which protrudes radially outwardly therefrom for sealing engagement against a bore periphery in the front end, or chuck portion, 61 (FIG. 7) of the handpiece 11, for preventing leakage of liquid from the surgical site rearward along the outside of the mounting hub into the handpiece 11. It will be understood that the chuck portion 61 of the handpiece 11 is shown somewhat schematically to more clearly illustrate the features of the invention.

In the preferred embodiment shown, the tool 12 is chucked in the handpiece chuck 61 by displacing axially the outer chuck part 87 rearward against a spring 66 back by the handpiece casing 20 (FIG. 7). The chuck portion 61 includes a bore 62 which then receives the rear portion 53 of the fixed mounting hub 31 (as well as the portion of the inner rotor 40 to the rear thereof). Rearward displacement of the tool 12 with the respect to the chuck portion 61 is positively stopped by abutment of the rear face of the circumferential rib 55 against a forward facing step 63 defining the rear end of a forward opening recess 64 communicating with the forward end of the bore 62. Thus the chuck recess 64 rearwardly receives the rib 55 fully thereinto. The chuck 61 here illustrated includes a latch member 65 (here for example a ball) normally cammed radially inward by a ramp on the surrounding outer chuck part 67 with part 67 normally urged forward by the spring 66. However, with the outer chuck part 67 displaced rearward from its FIG. 7 position, the ball 65 can float radially out beyond the perimeter of the tool ridge 55. Thus, upon rearward insertion of the tool 12 in the chuck portion 61, the ridge 55 easily pushes the ball 65 radially outward out of the way to allow such ridge 55 to move into rearward abutment with the chuck step 63. The user then releases the chuck outer part 67 and the latter is displaced forward its FIG. 7 position by the spring 66, thus positively camming the bell radially inward to its FIG. 7 position in front of the circumferential rib 55 of the tool 12. The front edge of the circumferential rib 55 is provided with circumferentially spaced substantially spherical notches 71 (FIGS. 6, 7 and 16) shaped and sized to receive the rear, radially inner portion of the ball 65, so as to urge the tool 12 rearward against the chuck step 63 and retain the tool 12 axially and circumferentially fixed in place in the chuck.

To remove the tool 12 from the chuck, one need merely again displace the chuck part 67 rearward, then displace the top 12 forward (the circumferential rib 55 camming the floating ball 65 radially outward out of its way) and release the chuck part 67.

The notches 71 prevent inadvertent rotation of the tool mounting hub 31 within the handpiece 11 due to interference with the ball 65 with the unnotched portions 72 of the forward edge of the circumferential rib 55.

Figure 16:
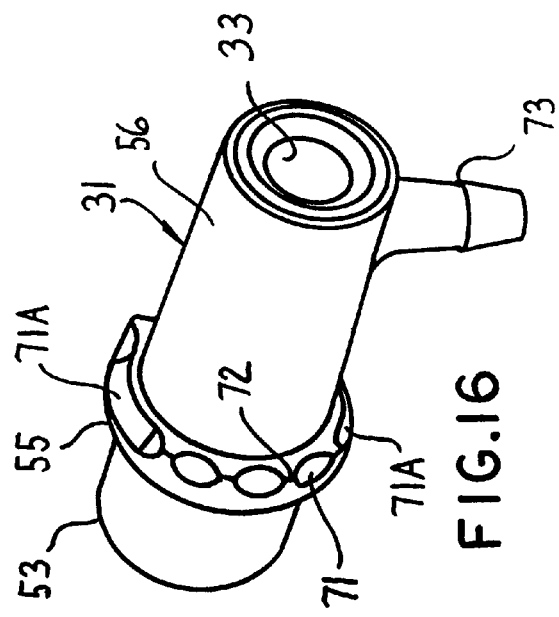
FIG. 16 is a pictorial view of the tubular mounting hub of the outer housing of the FIG. 4 cutter.

In the embodiment shown, one of the notches 71, namely one indicated at 71A in FIG. 16, is circumferentially elongate to permit limited angular displacement of the mounting hub 31 with respect to the handpiece, if the circumferentially elongate notch 71A is the one engaged by the ball 65.

It is contemplated that more than one radially inwardly resiliently biased ball 65 may be supplied and in the embodiment shown, three such balls are preferably provided in evenly circumferentially spaced (e.g. 120°) relation. As seen in FIG. 16, two circumferentially spaced elongate notches 71A are provided in the circumferential rib 55.

The mounting hub 31 has a substantially radially outward extending hollow fitting, here in the form of a nipple 73 (FIGS. 5, 6 and 16), near the front end thereof and spaced forward from the circumferential rib 55 and handpiece chuck portion 61 (FIG. 10). The fitting 73 includes a through passage 74 for irrigation liquid, extending through the radially outer end of the nipple 73 and thence radially inward therefrom into the central bore 33 of the mounting hub 31. See also FIG. 17. The outer end of the nipple 73 is connectable to communicate with an outflow hose portion, hereafter described at 204, of the tube set 14 (FIG. 1).

Figure 17:
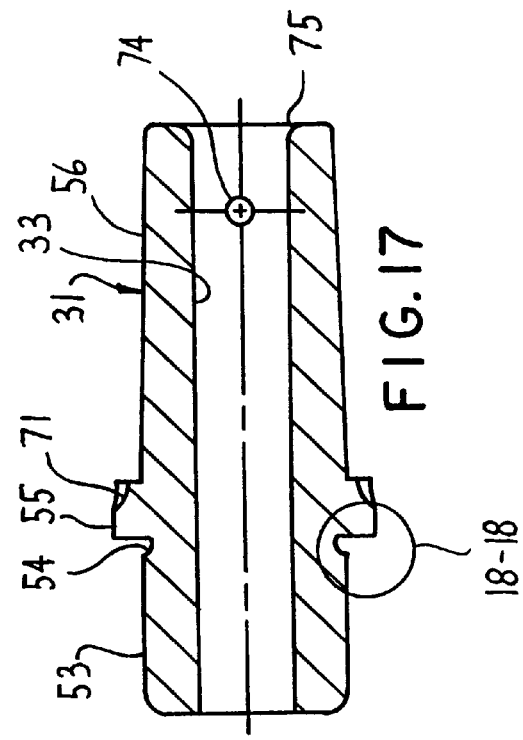
FIG. 17 is a central cross-sectional view thereof.
Figure 18:
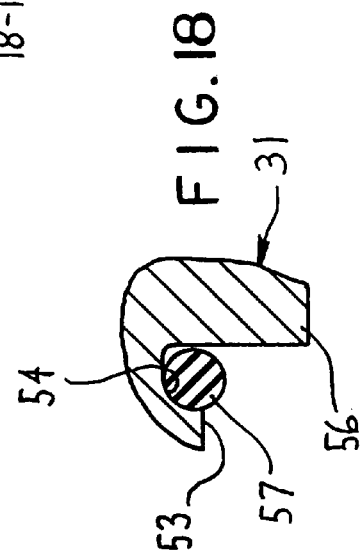
FIG. 18 is an enlarged fragment, indicated at 18—18 of FIG. 17.

The front end of the bore 33 is chamfered as indicated at 75 in FIG. 17 to facilitate installation of the rear end of the outer tube 32 rearwardly into the bore 33 of the mounting hub 31 to allocate same therein in the manner indicated in FIGS. 5 and 6.

The outer tube 32 (FIGS. 11–15) comprises an elongate cylindrical rearward portion 80 from which forwardly coaxially extends a substantially shorter hollow tubular nose piece 81. The nose piece is slightly lesser inner and outer diameter than the elongate cylindrical rearward portion 80 and is joined thereto by any convenient and conventional means, for example, integrally, as by radially inwardly deforming the nose piece, or by laser welding or the like of initially separate pieces 80 and 81. The joinder defines circumferential external and internal steps 82 and 83 (FIG. 13). While the front end of the nose piece 81 may be configured as desired, in the embodiment shown it is convexly rounded forward in a generally spherical manner as indicated at 84. Although the nose piece can be configured to perform a variety of surgical, patient tissue working operations, in the particular unit shown, the nose piece 81 is provided with a sloped planar relief defining the angled shearing outer window 46, same being provided with a sharp shearing edge 85 for shearing coaction with the above mentioned inner window 47 of the inner tube 42 hereafter discussed. The radial interior diameter reduction, or necking in, of the nose piece 81 with respect to the rearward cylindrical portion 80, provides a close radial shearing fit with the exterior of the front portion of the inner tube 42.

The elongate cylindrical rearward portion 80 of the outer tube 32 includes an irrigation liquid inlet port 90 (FIGS. 11 and 12) axially positioned to align with and be centered on the irrigation liquid through passage 74 of the nipple 73, when the mounting hub 31 is assembled on the outer tube 32. The irrigation liquid inlet port 90 is preferably substantially D-shaped, with the straight edge of the D-shape at the forward end of the port 90 and the curved portion of the port 90 extending rearward therefrom. The hole 90 is preferably formed in the outer tube 32 by wire EDM or, any other convenient means, such as by transverse (chordal) milling, with an appropriately shaped milling wheel perimeter cross section. The substantially D-shaped configuration of the post 90 facilitates snug telescoping of the rigid plastics mounting hub 31 over the rear end portion of the outer tube 32 during assembly by reducing any tendency of the edges of the hole 90 to gouge the inside of the mounting hub during relative axial motion therebetween as assembly is being carried out.

In the preferred embodiment, a heated metal outer tube 32 is pressed coaxially forward or rearward into a somewhat undersized bore 33 in a thermoplastics material mounting hub 31, which provides, after the metal tube cools, a rigid fixed coaxial joinder between tube 32 and hub 31.

Given a mounting hub 31 of thermoplastic material, insertion of a heated metal outer tube 31 tends to soften the engaged portion of the thermoplastics mounting hub to allow easy pressed insertion of tube into mounting hub, whereafter cooling of the tube allows the mounting hub to recontour its inner bore to closely fit and harden about the cooled metal tube. To further facilitate fixed connection of tube to hub, it may be desired to externally knurl, or otherwise surface roughen, the rear end portion of the outer tube 32 in spaced relation to the rear of the hole 90, as for example schematically and partially indicated at 92 in FIG. 15. Alternately, the knurling is extendably over the entire area in contact with the hub 31.

Upon rearward sliding of the rear end of the heated metal outer tube 32 into the bore 33 of the mounting hub 31, the sloped curved edge 91 of the rear portion of the hole 90 tends to slide rearward easily past the rear end of the through passage 74 (FIG. 6) without risk of distorting or partially closing same and so avoids the risk of reducing irrigation flow cross section through the assembled housing 30.

Figure 19:
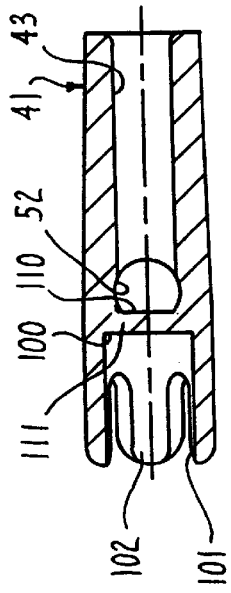
FIG. 19 is a pictorial view of a drivable rotor hub of the inner rotor of the FIG. 4 cutter.
Figure 20:
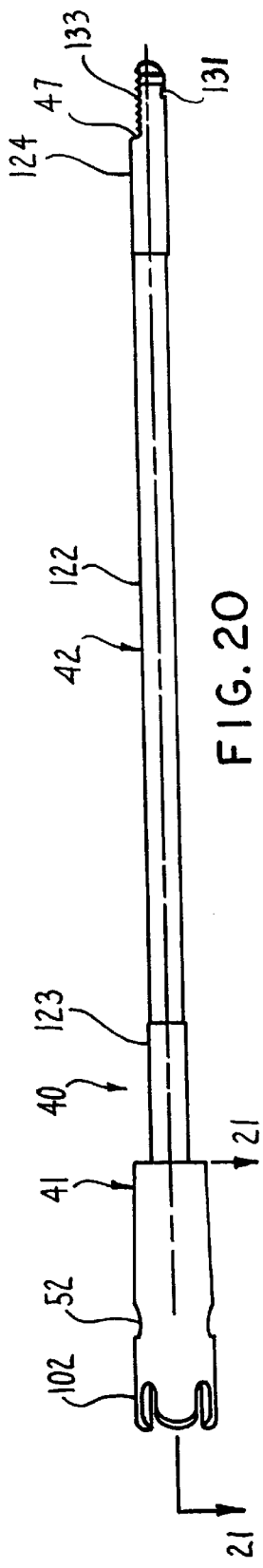
FIG. 20 is an elevational view of the inner rotor of the FIG. 4 cutter.

Turning now to the inner rotor 40 in more detail, the rotor hub 41 (FIGS. 19–21) has a preferably cylindrical, rear opening coaxial recess 100. The rear part of the recess 100 has diametrally opposed rear opening notches 101 (here two pair thereof) separated by rear extending fingers 102. The rear ends of fingers 102 are preferably rounded, at least in their radially outer parts and in the rear end portions of the notches 101.

Generally in the manner shown in U.S. Pat. No. 5,192,292, assigned to the assignee of the present invention, a coil compression spring 103 (FIG. 4) is received in and protrudes rearwardly (when at rest) from the recess 100 peripherally walled by the fingers 102. With the tool 12 chucked in the handpiece 11 (FIG. 1), the front end 104 of the shaft of the powered rotation source 15 inserts into the rotor hub recess 100 (FIG. 4) to compress the spring and thereby urge the inner rotor 40 forward with respect to the housing 30. A diametral cross-pin 105 has outer ends received in diametrally opposed ones of the notches 101 for rotatably driving the circumferentially flanking ones of the fingers 102 and thereby rotating the inner rotor 40.

Figure 21:
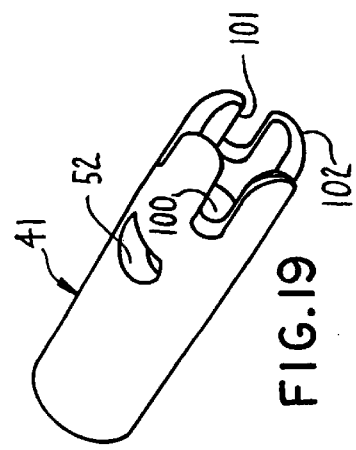
FIG. 21 is an enlarged central cross sectional view substantially taken on line 21—21 of FIG. 20.

The suction hole 52 preferably is substantially D-shaped, as seen in FIG. 21, with the flat edge 110 thereof rearmost and separated from the rear recess 100 by a transverse wall 111 which may thus be diametral, flat, and relatively thin. As seen in FIG. 5, the suction hole 52 extends diametrally through the rotor hub and the rear end portion of the inner tube 42 extends rearwardly part way into the suction hole 52 for direct communication of the suction bore 44 of the inner tube 42 with the transverse suction hole 52, and thereby with the suction source SU when the tool 12 is chucked in the handpiece as seen in FIG. 1.

The inner tube 42 comprises an elongate substantially cylindrical rearward portion 120 carrying a coaxial front end portion 121, which in a particular unit shown is closed except at the front portion of the window 47, the latter being formed in the elongate cylindrical portion 120, as seen in FIGS. 23 and 25. In the embodiment shown, the interior surface of the elongate cylindrical portion 120 defines the bore 44 and is substantially cylindrical, and hence of substantially constant diameter, throughout its length.

In contrast, the elongate intermediate outer periphery 122 of the inner tube 42 is of diameter reduced from, but coaxial with, the rear and front outer peripheral portions 123 and 124 of the periphery 122. Rear and front portions 123 and 124 act as rear and front radial thrust bearings, respectively, to rotatably support the inner tube 42 within the outer tube 32.

The front radial thrust bearing portion 124 is circumferentially interrupted by a longitudinal irrigation liquid channel 130 which communicates from the intermediate outer peripheral portion 122 of the inner tube substantially to the inner tube front end. An irrigation liquid port 131 (FIGS. 23–25) extends through the peripheral wall of the front outer peripheral portion 124 and communicates between the bore 44 of the inner tube and the longitudinal irrigation liquid channel 130. Preferably the port 131 is centered circumferentially on the channel 130 and both are diametrically opposed to the window 47. In the embodiment shown, the port 131 opens through the irrigation liquid channel 130 near the front end thereof and is spaced slightly rearward from the rounded front end portion 121.

In the preferred embodiment shown, the channel 130 is conveniently an axially elongate chordal flat in the outer periphery of the forward portion 124, which flat 130 extends rearward somewhat into the intermediate peripheral portion 122 of the inner tube and is of sufficient radial depth as to flatten the periphery of the reduced diameter intermediate portion 122. The port 131 and channel 130 each can be formed by any convenient means, e.g. EDM or a simple tangential grinding or milling pass across the periphery of the inner tube.

The port 131 is conveniently formed by a chordal flat 132 incised sufficiently deeply into the periphery of the inner tube 42 as to open into the bore 44. The chordal flat 132 is circumferentially somewhat wider than, and axially much shorter than, the chordal flat 130.

Although windows 47 of various forms are contemplated, in the embodiment shown in FIGS. 23 and 25, the window 47 through most of its length extends substantially along a chordal plane of the inner tube 42 and occupies close to but less than half the circumference of the inner tube 42. Also in the embodiment shown in FIGS. 23 and 25, the chordal edges of the window 47 are provided with teeth 133 spaced longitudinally therealong.

Figure 22:
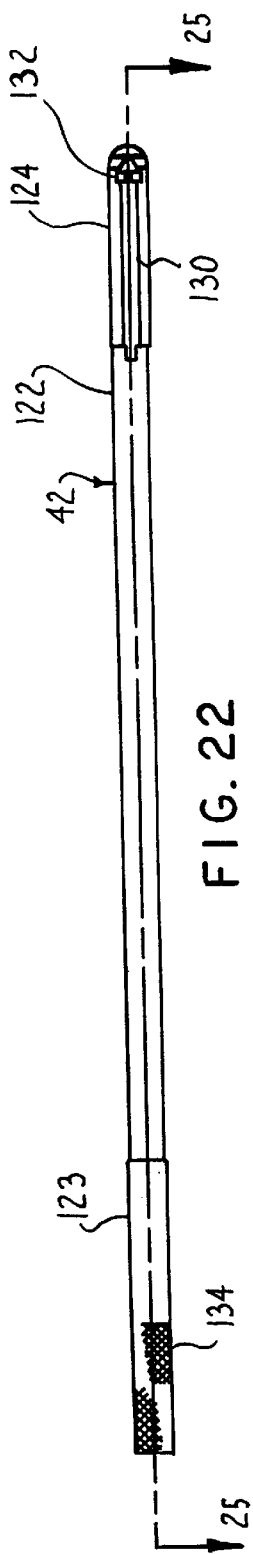
FIG. 22 is an elevational view of the inner tube of the FIG. 20 inner rotor, taken from the bottom thereof in FIG. 20.

The rear portion 123 of the inner tube 42 is telescopingly fixed in the front opening bore 43 of the rotor hub 41, as shown in FIG. 5, by any convenient means, for example in the manner above described with respect to fixing of the outer tube 32 in the mounting hub 31. For example, the rotor hub 41 is preferably of a thermoplastic material for receiving the heated rearward portion 123 of the inner tube 42 to, upon cooling, fixedly grip the latter. Again, to facilitate fixed gripping, the rearwardmost part of the inner tube rear portion 123 may be surface textured, as by knurling 134 (FIG. 22), if desired.

With the outer housing 30 and inner rotor 40 each assembled in the manner above discussed, the tool 12 can be assembled by simply inserting the inner tube 42 forwardly into the open rear end of the outer tube 32 and its surrounding mounting hub 31, in the manner generally indicated in FIGS. 4 and 5.

When thus assembled, and as seen in larger size in FIG. 5A, the front end portion of the inner tube is supported by rotating bearing contact of its front outer periphery 124 by the inward stepped nose piece 81 of the outer tube 32 across the bearing clearance gap 135 of approximately 0.001 inch. The rearward portion 123 of the inner tube 42 is supported rotationally by the rear end portion of the outer tube 32 across a bearing clearance gap 136 of approximately 0.0035 inch. The irrigation liquid inlet port 90 of the outer tube 32 supplies irrigation liquid radially inward to an annular fluid passage 140 having a radial thickness of about 0.007 inch. Irrigation liquid flow is represented by the arrows in FIG. 5A and passes forward through the annular flow passage 140, then through the longitudinal irrigation liquid channel 130 formed by the corresponding chordal flat, and then forward beyond the step 83 in the outer tube 32 and radially inward through the port 131 into the interior of the inner tube 42.

The assembled tool 12 is chucked, as above discussed, with the tool circumferential rib 71 trapped behind the balls 65 (FIG. 7) to hold the outer housing 30 of the tool 12 fixed in the handpiece chuck 61 and wherein the rear end of the rotor hub 41 and its spring 103 engage the rotatable shaft 104 and its drive pin 105 in the manner discussed above with respect to FIG. 4, for rotating the inner rotor 40 with respect to the outer housing 30 of the tool.

Irrigation liquid flow, in accord with the arrows in FIG. 3, passes radially inward through the port 131 in the inner tube and into the forward portion of the interior thereof opposite the windows 46 and 47. If suction is not applied to the inner tube 42, the irrigation liquid then flows out through the rotating inner tube window 46 and fixed outer tube window 47 into the surgical site SS for supplying the latter with irrigation liquid.

On the other hand, when suction is applied to the rear end of the inner tube 42, as in FIG. 2, such suction tends to pull rearward, through the inner tube 42, irrigation liquid and entrained surgical debris drawn through the periodically radially aligned windows 46 and 47 from the surgical site.

Figure 8:
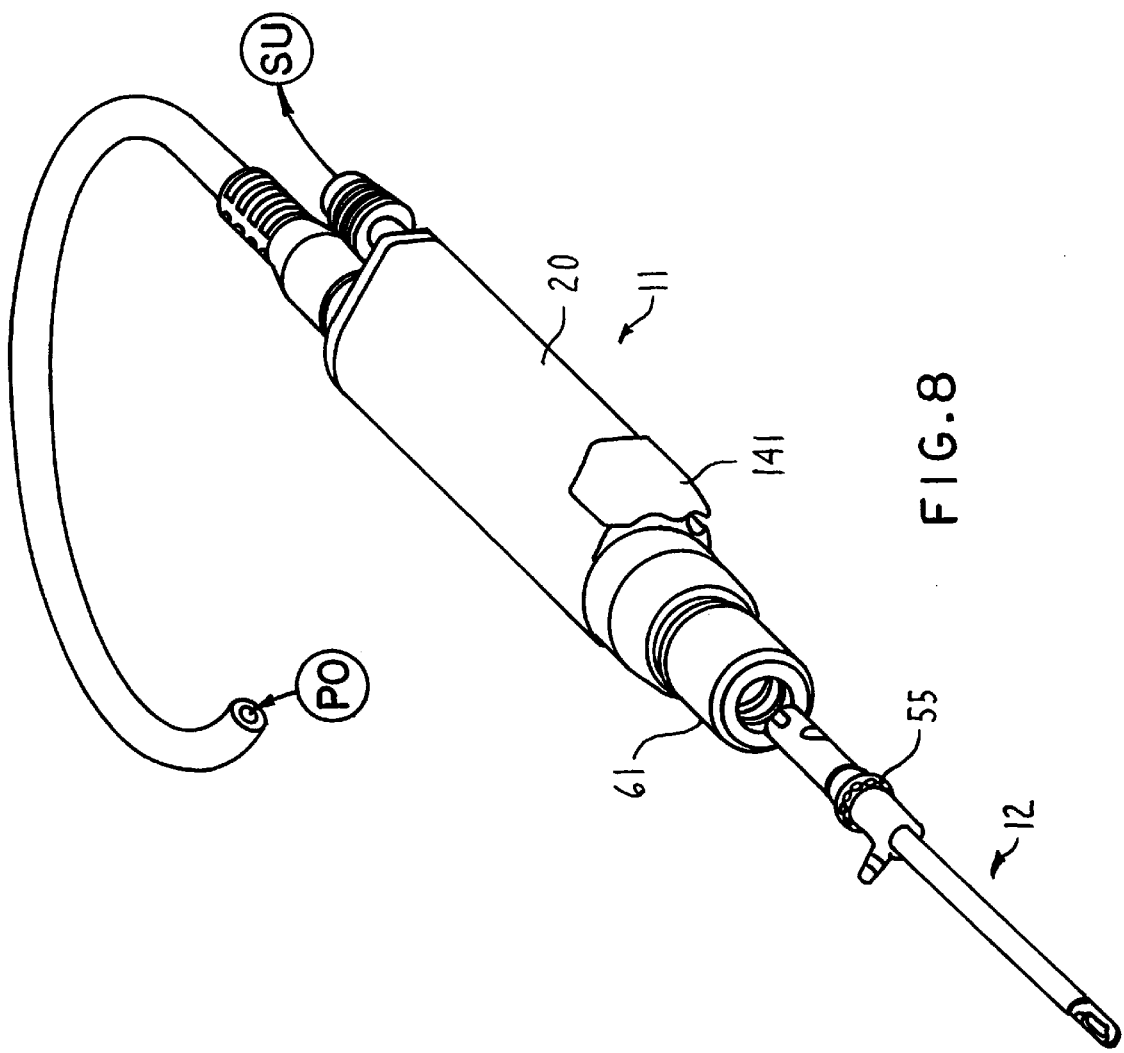
FIG. 8 is a fragmentary exploded view of the FIG. 1 handpiece and cutter, showing same positioned prior to insertion of the rear end of the cutter into the front end of the handpiece.

If desired, the handpiece 11 itself may be provided with the user operator control for controlling rotation of the tool 12 and/or suction in a conventional manner and for this purpose a user thumb actuable push button control 141 is shown in FIG. 8.

Figure 29:
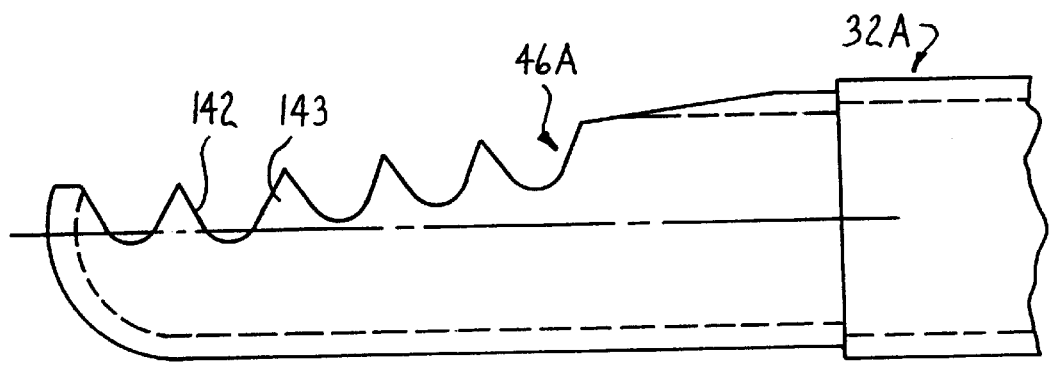
FIG. 29 is an enlarged fragmentary elevational view of the forward end of the fixed outer tube generally similar to the orientation of FIG. 13 but taken from the opposite side thereof and showing a modification of the cutting window.
Figure 30:
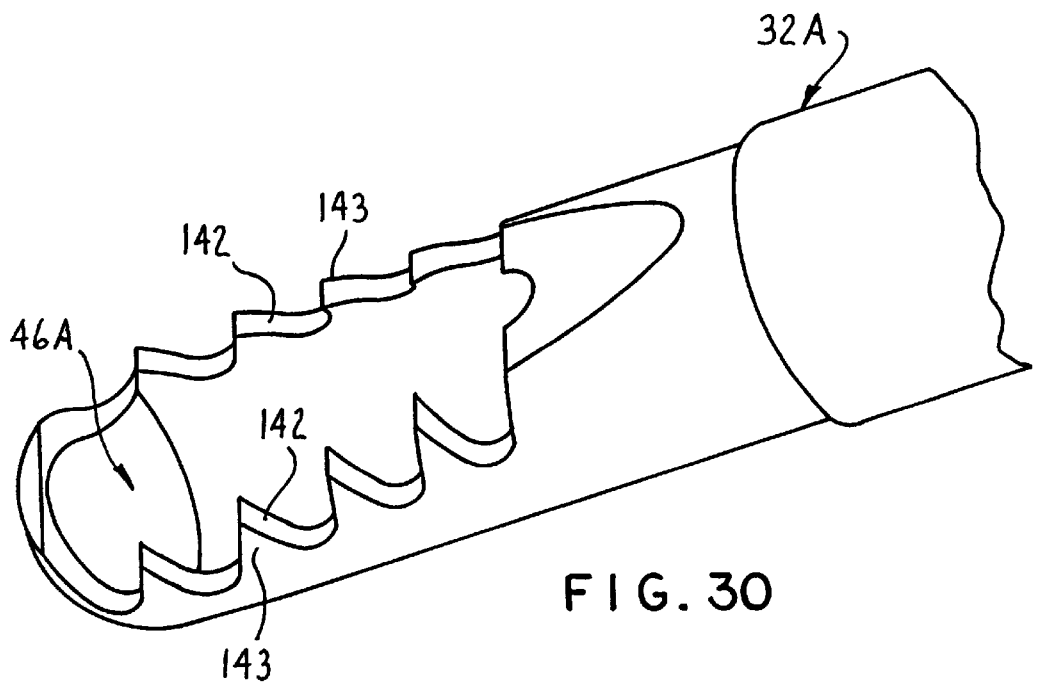
FIG. 30 is a pictorial view of the modified FIG. 29 device.

FIGS. 29 and 30 show a modified cutting window 46A of the fixed outer tube wherein the opposite sides of the window 46A of the outer tube 32A have a series of notches 142 formed therein, leaving the sides of the modified window 46A defined by a plurality of teeth separated by such notches 142. The teeth 142 coact with the teeth 133 in the window 47 of the rotating inner tube 42. It has been found by the Applicant that the toothed (at 143) window 46A of the modified outer tube 32A provides a more aggressive cutting action than the untoothed window 46 of the outer tube 32 of FIG. 15.

Irrigation liquid flow rearward from the irrigator inlet port 90 has not been significant, and thus is believed a result of the path of least resistance to irrigation flow being forward from the port. Thus, while no liquid seal rearward of port 90 has been needed, a modification is contemplated which, as shown for example in FIG. 5B, provides an annular seal member 144 (e.g. of Teflon(™) or other conventional seal material) sealingly interposed between the fixed housing 30B and inner rotor 40B (here between the opposed ends of the fixed and rotating hubs 31B and 41B), behind the port 90 (FIG. 5).

Turning now more particularly to the console 13 and tube set 14, the console 13 (FIGS. 35–38) includes a case 151 and a mounting plate 150 which forms a portion (the left front portion in FIG. 1) of the case 151. The mounting plate 150 is preferably of a rigid molded plastics material. The mounting plate 150 has a motor 152 (FIG. 37) mounted to extend fixedly rearwardly therefrom. The motor 152 is fixed on the mounting plate 150 through any convenient means, here including a fixed rigid carrier member 153. The motor 152 has a rotatable shaft 154 extending forward through a hole 155 in the mounting plate 150. A peristaltic pump rotor 160 is fixed on the shaft 154 for rotation therewith in front of the mounting plate 150.

In the embodiment shown, the rotor comprises axially opposed, preferably identical, generally triangular, front and rear roller carriers 161 and 162 (FIG. 37). The roller carriers 161 and 162 each comprise a substantially radially extending, generally triangularly plate 163 and plural (here 3) pairs of coaxially opposed stub shafts 164. In the embodiment shown, the carriers 161 and 162 are of molded plastic and the stub shafts 164 are recessed at their opposed free ends to minimize the amount of plastics material required. Each coaxially opposed pair of stub shafts 164 rotatably supports a generally spool-shaped, coaxial, peristaltic pump roller 165. The roller carriers 161 and 162 are fixed on the shaft 154 by any convenient means, for example by sandwiching axially between diametral through pins 170 fixedly diametrally extending from the motor shaft 154 adjacent front and rear ends of the shaft and engaging corresponding diametral depressions in the axially opposite sides of the plates 163. In this way, the carriers 161 and 162 are held against axial separation so as to reliably rotatably support the rollers 165 and are positively rotatably drive by the motor shaft 154 and thereby for orbiting the pump rollers 165 by rotation of the motor shaft 154. Thus, rotation of the motor shaft 154, in response to energization of the motor 152, rotates the peristaltic pump rotor 160 and thereby orbits the rollers 165 for peristaltic pumping with respect to the peristaltic pumping portion of the tube set hereinafter discussed.

To facilitate assembly, the front end of shaft 154 may be recessed and the front (outer shaft end) pin may be diametrally prefixed in an axial plug 169. The carriers 161, 162 and rollers 165 may first be installed on the motor shaft 154. Then, the pinned plug 169 is axially inserted and fixed (e.g. by adhesive) in the recessed front end of the motor shaft 154, to fix the carriers 161, 162 on the motor shaft 154.

The mounting plate 150 has a forward step 171 spaced below the pump shaft 154 (FIG. 35) with a concave semi-circular hollow 172 below the rotor 160 and sized and shaped to loosely accommodate the orbiting rollers 165.

An arcuate cam 173 protrudes fixedly forward from the mounting plate 150. The cam 173 is semi-circularly concave toward the rotor 160 and hence longitudinally (in FIG. 35 downward) along the mounting plate 150. The concave face 174 of the cam 173 faces toward and extends circumferentially close along just outside the orbit of the rollers 165 of the pump rotor 160. On the other hand, the front face 175 of the cam 173 is a sloping ramp-like surface angled to face forward and longitudinally away from the rotor 160 (upward in FIG. 35) for purposes appearing hereafter.

The mounting plate 150 (FIG. 35) has parallel, longitudinally extending (extending vertically in FIG. 35), laterally spaced slots 180 therethrough. The bottom portions of the slots 180 are spaced on opposite sides of the cam 173 and extend at least to the bottom thereof (here slightly below same). Substantially at the level of the top of the cam 173, the slots 180 widen away from each other to form widened mouths 181.

Recesses 182 in the front face of the mounting plate 150 are well spaced above the cam 173 and extend upward in slightly vertically overlapping fashion above the slots 180. The recesses 182 are laterally spaced from each other and laterally spaced inboard of the slots 180. The space between the recesses 180 is approximately the width of the cam 173, here slightly greater. The recesses 182 have laterally opposed, laterally inwardly projecting, wedge shaped portions 183, including laterally inward and upward facing, angled ramps 184 terminating in downward facing steps 185.

The mounting plate 150 also has laterally spaced, parallel, longitudinally aligned, guide grooves laterally spaced closer to the recesses 182 than to each other, longitudinally overlapping both the recesses 182 and slots 180, and overlying, in vertically spaced relation, the cam 173.

The tube set 14 includes a cassette 190 (FIGS. 1 and 31–34). The cassette has a body 191 having longitudinally spaced top and bottom ends 192 and 193 and laterally spaced sides 194. The body 191 has a plate-like front wall 195 bounded by the ends 192 and 193 and sides 194. The body 191 includes a concave backing wall 200 (FIGS. 32 and 34) which extends rearward from the front wall 195 thicknesswise of the body 191. The concave backing wall 200 is semi-circular and opens concavely toward one end of the body, here the bottom end 193.

Figure 32:
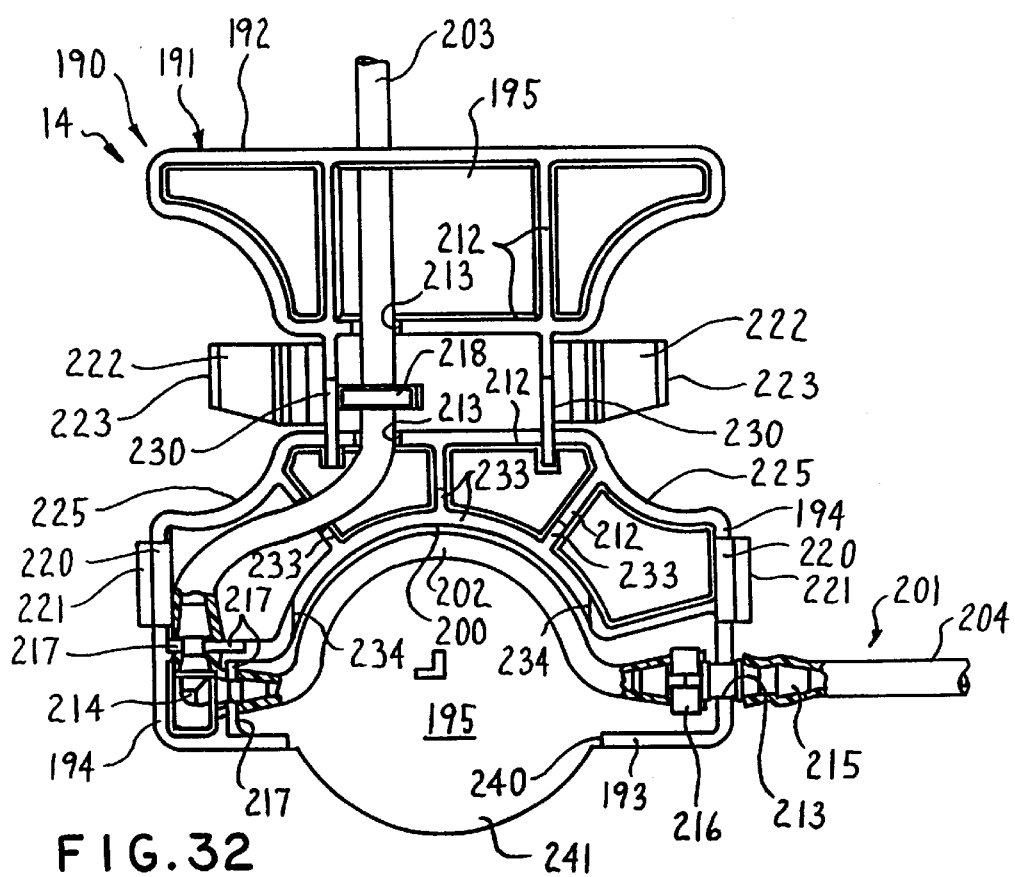
FIG. 32 is a rear view of the FIG. 31 cassette.
Figure 34:
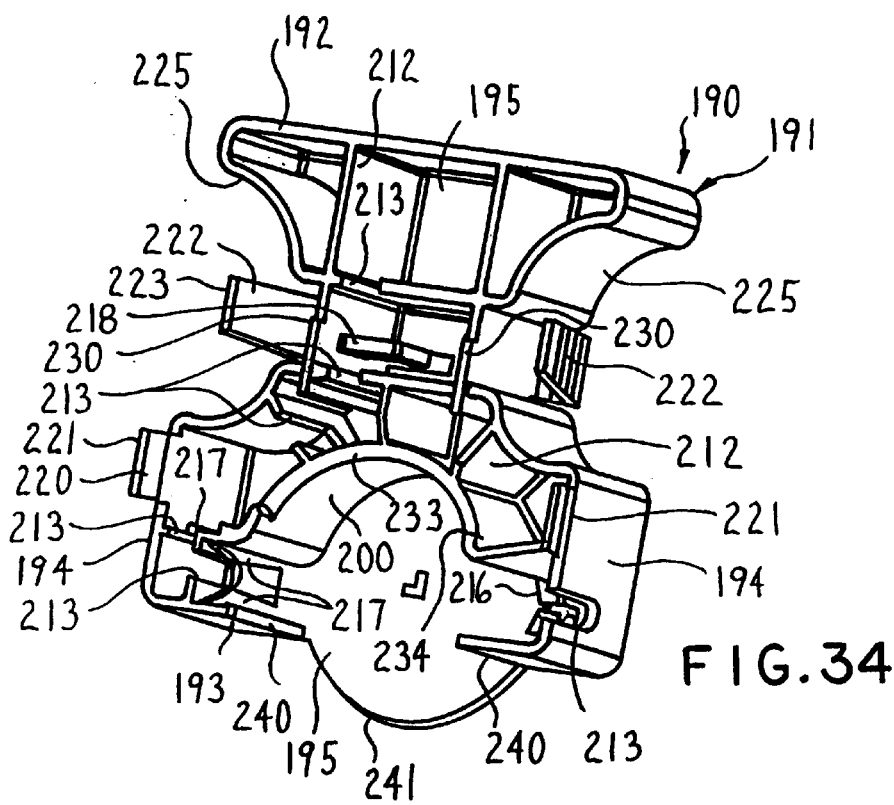
FIG. 34 is a similar pictorial view of the rear of the FIG. 33 cassette showing primarily the rear and left side thereof.
Figure 35:
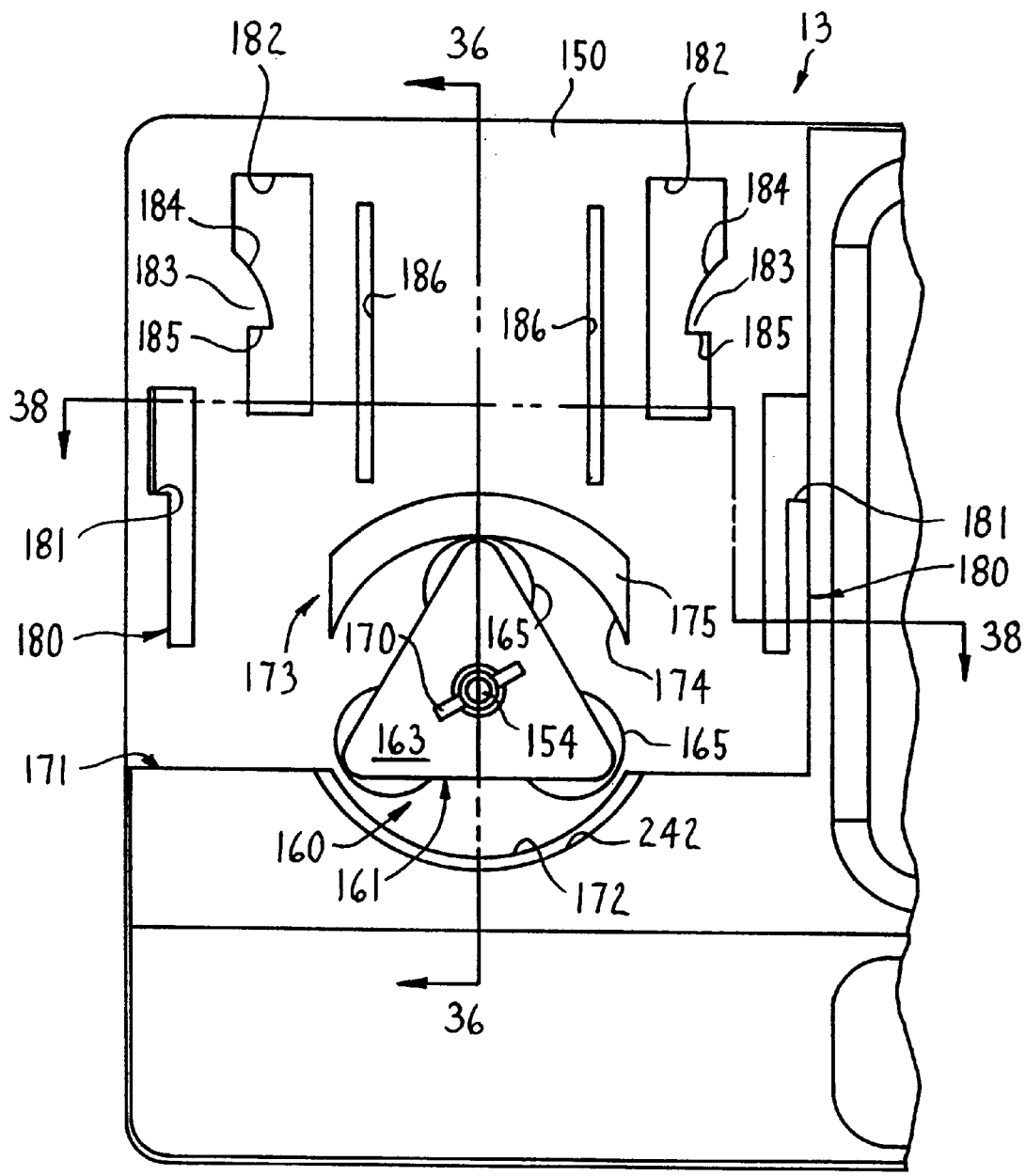
FIG. 35 is a fragmentary front view of the FIG. 1 console showing the peristaltic pump mounting plate with the FIG. 1 and 31 cassette removed.

The cassette body, as seen from the rear in FIGS. 32 and 34, is provided with plural reenforcing ribs 212 extending rearward from the front wall 195 to provide adequate strength to the body 191 while limiting the amount of material required. Such body is preferably formed by molding of a suitable plastics, hardenable material.

A peristaltic pumping hose 201 (FIG. 32) has a pumping portion 202 backed by the concave backing wall 200 and inflow and outflow portions 203 and 204 respectively extending from the cassette 190 and flanking the pumping portion 202. The inflow portion 203 of the pump hose 201 is provided with a suitable connector 210 at its free, upper end, for connection in a conventional manner to a irrigation liquid source such as the irrigation liquid bag IB in FIG. 1 and may be provided with a conventional removable clamp 211 for controlling flow from the bag IB.

The inflow hose portion 203 is led down into the cassette body 191 through a hole 205 in the cassette body top wall 192. An L-shaped keeper bar 218 (FIGS. 32 and 34) fixedly extends from one side wall 194 of the body 191 (the left side wall in FIGS. 32 and 34) intermediate the top most two lateral ribs 212 and opens forward toward the hose portion 203 to prevent its rearward escape from the adjacent notches 213. The inflow hose 203 is led through notches 213 in various of the ribs 212 down and to one side (the left in FIG. 32) of the downward opening concave backing wall 200 and sealingly and fixedly connects to an elbow 214 at one of the notches 213 in the adjacent rib 212. The other end of the elbow 214 points laterally into the space below the downwardly concave backing wall 200 and sealingly and fixedly connects to the left (in FIG. 32) end of the flexible peristaltic pumping hose 202. Opposed slightly rearward converging steps 217 extend rearward adjacent the corresponding notches 213 in the lower left (FIGS. 32 and 34) corner of the body 191 where the hoses 203 and 202 fixedly and sealingly interconnect by sleeving over the grooved ends of the elbow 214. The convergent pairs of steps 217 each form an undercut into which the corresponding end portion of the corresponding hose 203 or 202 is forcibly and resiliently forwardly pressed at a point where the corresponding hose passes over an annularly grooved portion of the elbow 214, so as to frictionally and through an interference fit tend to prevent rearward escape of the elbow 214 and corresponding hose ends of the hoses 202 and 203 out of the body 191.

In the embodiment shown, a straight line fitting 215 fixedly and sealingly connects the hose portions 202 and 204 (here at the right side of the body 191 as seen from the rear in FIG. 32). A preferably integral, U-shaped undercut spring clip 216 extends rearward from the cassette front wall 195, as seen in FIGS. 32 and 34. The spring clip 216 grips snugly, in snap fit fashion, the soft deformable hose pumping portion 202 where it surrounds a grooved portion of the straight line fitting 215. The fitting 215 is thus fixedly held in place on the cassette body 190. The outflow hose 204 extends laterally from the cassette body 190 by means of another notch 213 rearward opening in the corresponding side 194 of the cassette body.

The cassette has laterally spaced legs laterally flanking the concave backing wall 200 (FIG. 34) and spaced on opposite sides thereof. The legs 220 are located between the ends 192 and 193 of the body 191 adjacent the central portion of the backing wall 200. The legs 220 extend rearward from the body sides 194. Feet 221 on the rear ends of the legs 220 extend laterally (here outwardly) therefrom for blocking forward displacement of the cassette away from the mounting plate 150 of the console as hereafter discussed.

The cassette further has a laterally spaced resilient leaf spring-like arms 220 extending rearward from the body 191 and angled laterally rearwardly and away from each other. The arms have rear tips 223 for blocking longitudinal displacement of the cassette 190 with respect to the console mounting plate 150. The laterally outer faces of the arms 220 are preferably textured as indicated at 224 (for example by means of grooves or ridges transverse to the length of the arms) to facilitate gripping between the thumb and a finger of the user for squeezing, and thereby bending, the arms 223 laterally toward each other to thereby bring the tips 223 laterally closer to each other. In the preferred embodiment shown, the arms 222 are molded integrally with the body 191 and connect therewith at the front face 195, the arms 222 extending rearward an elongate, angled fashion so as to protrude and somewhat beyond the rear extent of the body. In the preferred embodiment shown, the body sides 194 are necked in laterally toward each other as indicated at 225 to form laterally outwardly concave recesses, such that the arms 222 are contained laterally in such recesses 225 and their tips 223 are, at rest, substantially closer together laterally than are the feet 221.

Figure 31:
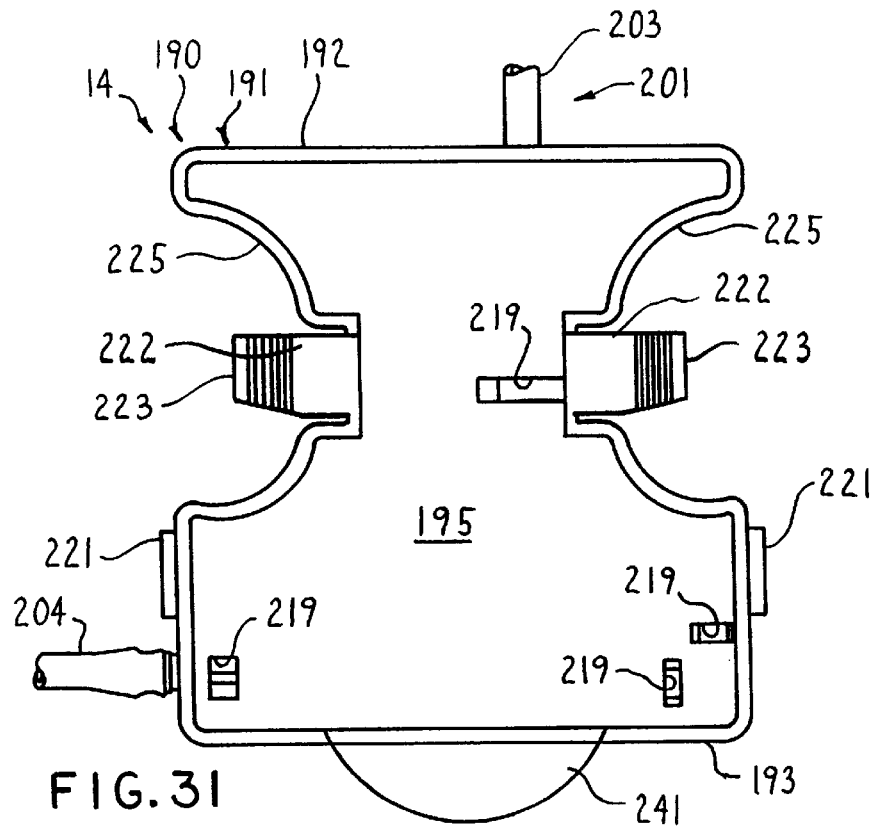
FIG. 31 is a front view of a pump cassette of the kind shown installed in pumping position on the FIG. 1 pump console.
Figure 33:
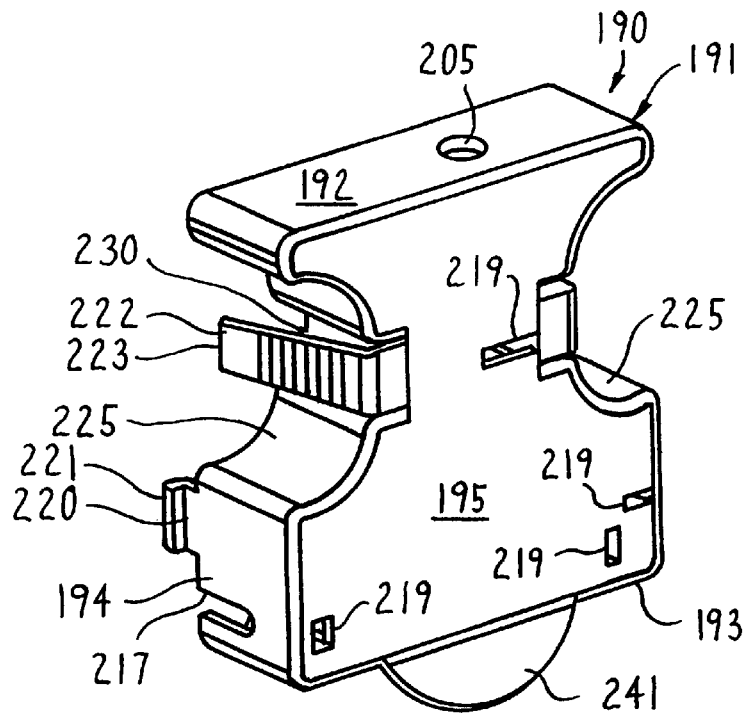
FIG. 33 is a pictorial view of the FIG. 31 cassette taken from the angle to show the top, left side and front thereof.

Holes 219 in the plate-like front wall 195 of the body 191 are located in front of the above described spring clip 216, rearward convergent step pairs and L-shaped keeper bar 218, as indicated in FIGS. 31 and 33, and are here left by special mold inserts (not shown) which are placed to form the spring clip 216, step pairs 217 and L-shaped keeper bar 218 during the molding of the cassette 190.

The cassette body 191 further includes a pair of parallel, longitudinally (vertically in FIG. 34) aligned, guide ridges 230 which extend rearward from the rear plane of the cassette body 192. In the preferred embodiment shown, the guide ridges 230 are rearward extensions of the sides 194 at the minimum separation of such sides in the recesses 225. The guide ridges 230 are thus, in the embodiment shown, flanked at least at their top portions by the arms 222, as seen in FIG. 32.

The concave backing wall 200 in its major central portion has a relieved and sloped rear edge 233, which is sloped to face rearward and downward (in FIG. 32) at an angle complementary to the sloped front face 175 of the arcuate cam 173 on the mounting plate 150 of the console. The sloped relieved rear edge 233 extends upward and rearward into ones of the reenforcing ribs 212 which converge toward and back the top of the concave backing wall 200. The relieved sloped portion of the rear edge 233 of the concave backing wall 200 extends almost the entire width thereof, in the embodiment shown ending at 234 at a sufficient lateral width to clear the lateral ends of the arcuate cam 173 on the mounting plate 150 of the console.

The central portion 240 (FIG. 32) of the cassette bottom 193 is open to clear the orbiting pump rollers 165. A convexly rounded portion 241 of the cassette plate-like front wall 195 extends down below the cassette bottom 193 to cover the orbit of the pump rollers 165 and to fit snugly in a front edge recess 242 (FIGS. 35 and 36) of the hollow 172 at the bottom of the mounting plate 150 of the console.

OPERATION

In the preferred embodiment shown, the tube set 14 and tool 12 are each prepackaged, disposable, single use, presterilized (by the manufacturer) devices, the handpiece 11 is sterilizable, and the handpiece and console 13 are reusable, multiple use devices.

Prior to use, the console 13 is located in the surgical operating room remote from the operating table (or other patient support) and is connected to a suitable electric power source EP (FIG. 1) at least for powering the peristaltic pump motor 152, as well as any other control functions that may be provided, e.g., as indicated by the dotted lines 22 and 23, control of the handpiece power source PO and suction source SU.

The tube set 14 is readied for use (typically by removal from a sterile package). The cassette 190 can then be installed on the mounting plate 150 of the console 13. To that end, the cassette 190 is moved forward into contact with the front of the mounting plate 150 with the cassette feet 221 entering the mouths 181 of the mounting plate slots 180. In this position, the rear of the cassette body 191 abuts the front face of the mounting plate 150, the tips 223 of the cassette arms 222 lie in the upper portions of the mounting plate recesses 182 above the wedge shaped portions 183, the cassette guide ridges 230 lie in the upper portions of the mounting plate guide grooves 186 and the cassette concave backing wall sloped rear edge 233 is spaced above the mounting plate arcuate cam 173.

The user then completes installation of the cassette 190 on the mounting plate 150 by simply moving the cassette downward on the mounting plate into its operative position shown in FIGS. 36–38.

Thus, the cassette legs 220 move downward in the mounting plate slots 180 below the mouths 181 thereof with the feet 221 trapped behind the mounting plate. The sloped front face 175 of the mounting plate arcuate cam 173 cams the hose pumping portion 202 forward onto the center of the rollers 165 (FIG. 37), thus insuring the pumping hose portion 202 does not get caught between the rollers 165 and the mounting plate 150.

Also during such downward cassette movement, the tips 223 of the arms 222 of the cassette ride the ramps 184 downward and inward, and finally spring laterally outwardly apart to lodge snugly under the mounting plate steps 185 to thereby lock the cassette 190 against unintended upward movement along the mounting plate 150.

The downward movement of the cassette 190 on the mounting plate 150 is in part guided by movement of the cassette guide ridges 230 downward in the mounting plate guide grooves 186 to a lower position therein.

With the cassette 190 thus installed on the mounting plate 150, in its operative position shown in FIGS. 1 and 36–38, the orbit of the pump rollers 165 is covered in front by the plate-like front wall 195 and convex rounded portion 241 thereof, of the cassette body 191, with the bottom edge of the convexly rounded portion 241 snugly received in the front edge recess 242 of the mounting plate hollow 172. Also in this installed position, the cassette concave backing wall 200 is flush with and extends forward from the downward facing arcuate cam concave face 174 of the backing plate 150 to provide an essentially continuous downwardly concave surface overlying the pump rotor 160 as generally indicated in FIGS. 36 and 37. This enables the pump rollers 165 to compress the hose pumping portion 202 against the cassette concave backing wall 200 as indicated in FIG. 37.

To ready same for use, the handpiece 11 is connected through the cable 21 to the power and suction sources PO and SU respectively, as seen in FIG. 1. A tool 12 may then be chucked in the handpiece 11 and the irrigation outflow hose 204 from the cassette 190 may then be connected, as indicated at 73, to the irrigation liquid inflow fitting of the tool 12. If desired, the outflow hose portion 204 may be secured to the body of the handpiece 11 by any convenient releasable clip means, not shown. The irrigation liquid inflow hose portion 203 may then be plugged on at 210 into a conventional irrigation liquid supply bag IB.

In surgical use, the peristaltic pump, defined by the cassette 190 and pump rotor 160 can be operated to supply irrigation liquid to the tool 12 and therethrough to the surgical site SS (FIG. 1). The peristaltic pump can be operated continuously by continuous energization of its motor 152 or discontinuously by turning on and off its motor 152. Turning on and off of the peristaltic pump motor may be accomplished by means near the surgical site such as a user operated foot switch or the like or by suitable switching on the console 13 in a conventional manner. If desired, means (not shown) may be provided on the outflow hose 204 to close or open flow therethrough and such means may be provided close to or on the handpiece for convenient use.

In use, the tool inner rotor 40 is rotated by the powered rotation source 15 of the handpiece 11, while the tool housing 30 is fixed with respect to the handpiece outer casing held by the surgeon. The rotating inner tube 42 thus rotates its inner window 47 repetitively passed the outer window 46 (FIGS. 2–4) of the outer tube 32 to accomplish a shearing type tissue cutting action. Tissue working can be accomplished with a variety of window configurations at 46, 47, including that shown in FIG. 4. For example, a more aggressive tissue cutting action can be accomplished by substituting the modified outer tube window configuration at 46A of FIGS. 29 and 30, with its teeth 142 in rotating cutting cooperation with the teeth 133 on the inner tube window 47.

As above discussed with respect to FIGS. 2 and 3, irrigation flow may be combined with suction flow (FIG. 2) or used alone to provide irrigation liquid to the surgical site.

As to the latter, and as schematically shown in FIG. 3, irrigation liquid flow through the fitting 73 and the annular flow space between the inner and outer tubes and thence through the port 131 provides irrigation liquid to the inside of the inner tube near its front end and thereby allows outflow of such irrigation liquid to the surgical site SS, through the windows 46 and 47 as they periodically mesh. On the other hand, when it is desired to remove debris from the surgical site, e.g. after cutting, provision of suction rearward through the inner tube 42 (as schematically indicated by arrows in FIG. 2) draws at least some of the irrigation liquid flowing into the inner tube through the hole 131 rearwardly along the inner tube to entrain and thereby retrieve unwanted debris from the surgical site SS.

The irrigation flow path between the inner and outer tubes has been described in detail above with respect to FIG. 5A, for example, and need not be repeated, as has the assembly of the tool 12 and its installation and removal from, the handpiece 11.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical irrigation peristaltic pump system for supplying and irrigating surgical instrument from an irrigation liquid source said pump system compressing:

a console including a mounting plate and a peristaltic pump rotor rotatably supported on said mounting plate, said rotor carrying hose compression rollers;

a tube set including a cassette having a body in turn having longitudinal and lateral and wideness dimensions, said body including ends spaced longitudinally thereon and sides spaced laterally thereon and a concave backing wall extending rearwardly thicknesswise of said body and concavely opening toward one end of said body, a peristaltic pump hose having a pumping portion backed by said concave backing wall and inflow and outflow portions extending from said cassette and flanking said pumping portion, means for connecting said hose inflow and outflow portions respectively to an irrigation liquid source and an irrigated surgical tool, said cassette being releasably fixable on said mounting plate in a peristaltic pump operative position in which said hose compression rollers compress said hose pumping portion against said concave backing wall, said console and cassette respectively including relatively engagable means for fixing said cassette on said console, said cassette being a single integral piece.

2. The apparatus of claim 1 in which said cassette has laterally spaced legs laterally flanking said concave backing wall and spaced on opposite sides thereof and located between said ends of said body adjacent a central portion of said concave backing wall, said legs extending rearward from said body and having feet for blocking forward displacement of said cassette away from said mounting plate.

3. The apparatus of claim 2 in which said console mounting plate has parallel laterally spaced slots of width to snugly slidably receive said legs with said feet trapped behind said mounting plate and mounting said cassette on a front of said mounting plate, said slots having widened mouths for rearward insertion of said feet therethrough.

4. The apparatus of claim 1 in which said cassette has laterally spaced resilient leaf spring-like arms extending rearward from said body and angled with respect to each other and having means for blocking longitudinal displacement of said cassette with respect to said mounting plate.

5. The apparatus of claim 4 in which said console mounting plate has parallel laterally spaced wedge-shaped portions including angled ramps for camming said arms laterally in opposite directions with respect to each other during longitudinal installing movement of said cassette on said console, and longitudinally facing steps positively blocking reverse longitudinal removing displacement of said cassette from said console.

6. The apparatus of claim 1 in which said cassette body has a rearward extending longitudinally aligned guide ridge.

7. The apparatus of claim 6 in which said console mounting plate has a longitudinally aligned guide groove for receiving said cassette body guide ridge and therewith for guiding longitudinal installing and removing displacement of said cassette body with respect to said mounting plate.

8. The apparatus of claim 1 in which said cassette has a longitudinally sloped rear edge on said concave backing wall, the slope of said rear edge facing toward the rear and longitudinally opening in the direction of said concave backing wall.

9. The apparatus of claim 8 in which said console mounting plate comprises an arcuate cam with a longitudinally sloped front face, said sloped front face facing forward and longitudinally in a direction complementing and cammingly engaging said sloped rear edge of said cassette backing wall rear edge upon longitudinal displacement of said cassette along said console mounting plate in a direction to bring said cassette concave backing wall toward said pump rotor to compress said pump portion of said hose therebetween.

10. A disposable single use surgical irrigation liquid tube set including a pump cassette replaceably engagable with a reusable peristaltic pump console of a kind having a peristaltic pump rotor carrying hose compression rollers for pumping surgical irrigation liquid to a surgical site, said tube set comprising:

a cassette having a body including a concave backing wall extending rearwardly thicknesswise of said body and concavely opening toward one end of said body;

a peristaltic pump hose having a pumping portion backed by said concave backing wall and inflow and outflow portions extending from said cassette and flanking said pumping portion;

means for connecting said hose inflow and outflow portions respectively to an irrigation liquid source and an irrigated surgical tool, said cassette being releasably fixable on a peristaltic pump console in a peristaltic pump operative position, said cassette including means integral therewith for engaging and fixedly mounting said hose on said cassette.

11. The apparatus of claim 10 in which said cassette body is substantially hourglass-shaped in front profile and has narrowed side portions defining laterally opening recesses, said cassette having means for releasably longitudinally locking said cassette in a desired location on a peristaltic pump console and defining a pair of laterally spaced spring arms pinchable toward each other to unlock said cassette and enable said cassette to be longitudinally displaced on a peristaltic pump console.

12. The apparatus of claim 10 in which said concave backing wall has a rear edge which is sloped toward the end of said cassette toward which said concave backing wall opens.

\* \* \* \* \*